US006586223B1

(12) United States Patent
Sikorski et al.

(10) Patent No.: US 6,586,223 B1
(45) Date of Patent: Jul. 1, 2003

(54) SUBTILISIN PROTEASE VARIANTS HAVING AMINO ACID SUBSTITUTIONS IN DEFINED EPITOPE REGIONS

(75) Inventors: Elizabeth Ellen Sikorski, Fairfield, OH (US); Donn Nelton Rubingh, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/618,573

(22) Filed: Jul. 18, 2000

Related U.S. Application Data

(60) Provisional application No. 60/144,980, filed on Jul. 22, 1999.

(51) Int. Cl.$^7$ .......................... C12N 9/54; C12N 15/57; C12N 15/75; C11D 3/386

(52) U.S. Cl. ...................... 435/220; 435/69.1; 435/221; 435/222; 435/252.3; 435/320.1; 435/471; 536/23.2; 510/350

(58) Field of Search ................................ 435/221, 222, 435/69.1, 471, 252.31, 320.1; 510/350; 524/267; 536/23.2

(56) References Cited

U.S. PATENT DOCUMENTS

| | | | | | |
|---|---|---|---|---|---|
| 4,179,337 | A | | 12/1979 | Davis et al. | 435/181 |
| 4,248,786 | A | | 2/1981 | Batz | 260/326 |
| 4,266,031 | A | | 5/1981 | Tang et al. | 435/188 |
| 4,556,554 | A | | 12/1985 | Calvo | 424/70 |
| 4,732,863 | A | | 3/1988 | Tomasi et al. | 436/547 |
| 4,760,025 | A | | 7/1988 | Estell | 435/222 |
| 4,980,288 | A | | 12/1990 | Bryan | 435/222 |
| 5,122,614 | A | | 6/1992 | Zalipsky | 548/520 |
| 5,133,968 | A | | 7/1992 | Nakayama | 424/401 |
| 5,155,033 | A | * | 10/1992 | Estell et al. | 435/221 |
| 5,208,158 | A | | 5/1993 | Bech et al. | 435/219 |
| 5,230,891 | A | | 7/1993 | Nakayama | 424/401 |
| 5,324,844 | A | | 6/1994 | Zalipsky | 548/520 |
| 5,414,135 | A | | 5/1995 | Snow et al. | 568/30 |
| 5,446,090 | A | | 8/1995 | Harris | 525/54 |
| 5,470,733 | A | * | 11/1995 | Bryan et al. | 435/222 |
| 5,500,364 | A | * | 3/1996 | Christianson et al. | 435/221 |
| 5,543,302 | A | | 8/1996 | Boguslawski et al. | |
| 5,567,601 | A | * | 10/1996 | Bryan et al. | 435/222 |
| 5,631,322 | A | | 5/1997 | Veronese et al. | 525/54.1 |
| 5,658,871 | A | | 8/1997 | Batenburg et al. | 252/174.12 |
| 5,707,848 | A | * | 1/1998 | Bryan et al. | 435/222 |
| 5,741,694 | A | * | 4/1998 | Hastrup et al. | 435/221 |
| 5,766,898 | A | | 6/1998 | Loevburg | |
| 5,856,451 | A | | 1/1999 | Olsen et al. | 530/402 |
| 5,972,339 | A | | 10/1999 | Walker | |
| 5,985,264 | A | | 11/1999 | Metzger et al. | |
| 6,060,546 | A | * | 5/2000 | Powell et al. | 524/267 |
| 6,197,567 | B1 | * | 3/2001 | Aaslyng et al. | 435/221 |
| 6,218,165 | B1 | * | 4/2001 | Estell et al. | 435/221 |

FOREIGN PATENT DOCUMENTS

| | | | |
|---|---|---|---|
| DE | 2 206 826 | | 8/1973 |
| EP | 0 130 756 | A1 | 1/1985 |
| EP | 0 215662 | | 3/1987 |
| EP | 0 260 105 | B1 | 3/1988 |
| EP | 0 398 539 | B1 | 11/1990 |
| EP | 0 405 901 | A | 1/1991 |
| EP | 0 471 125 | A1 | 12/1992 |
| EP | 0 516200 | | 12/1992 |
| EP | 0 584876 | | 3/1994 |
| EP | 0 251446 | B1 | 12/1994 |
| EP | 0 816381 | | 1/1998 |
| WO | WO 87/04461 | A1 | 7/1987 |
| WO | WO 87/05050 | A1 | 8/1987 |
| WO | WO 88/07578 | A1 | 10/1988 |
| WO | WO 88/08028 | A1 | 10/1988 |
| WO | WO 88/08033 | A1 | 10/1988 |
| WO | WO 88/08164 | A1 | 10/1988 |
| WO | WO 88/08165 | A1 | 10/1988 |
| WO | WO 92/10755 | | 6/1992 |
| WO | WO 93/15189 | | 8/1993 |
| WO | WO 93/19731 | | 10/1993 |
| WO | WO 93/19732 | | 10/1993 |
| WO | WO 93/25667 | A1 | 12/1993 |
| WO | WO 94/04193 | | 3/1994 |
| WO | WO 95/07991 | A2 | 3/1995 |
| WO | WO 95/10615 | | 4/1995 |
| WO | WO 95/20039 | A2 | 7/1995 |
| WO | WO 95/29979 | | 11/1995 |
| WO | WO 95/30010 | | 11/1995 |
| WO | WO 96/09396 | A1 | 3/1996 |
| WO | WO 96/16177 | | 5/1996 |
| WO | WO 96/17929 | | 6/1996 |
| WO | WO 96/40791 | | 12/1996 |
| WO | WO 96/40792 | | 12/1996 |

(List continued on next page.)

OTHER PUBLICATIONS

Atassi, M.Z., et al., "Structure, Activity, and Immune (T and B Cell) Recognition of Botulinum Neurotoxins", Critical Reviews in Immunology, vol. 19, pp. 219–260 (1999).

Blaser, K., "Allergen Dose Dependent Cytokine Production Regulates Specific IgE and IgG Antibody Production", New Horizons in Allergy Immunotherapy, Sehon et al. (Ed.) Plenum Press, N.Y. (1996).

(List continued on next page.)

*Primary Examiner*—Ponnathapu Achutamurthy
*Assistant Examiner*—William W. Moore
(74) *Attorney, Agent, or Firm*—Laura L. Frieko; Brent M. Peebles; Dara M. Kendall

(57) ABSTRACT

The present invention relates to variants of subtilisin-like proteases having decreased immunogenicity relative to their corresponding wild-type proteases. More particularly, the present invention relates to variants having a modified amino acid sequence of a wild-type amino acid sequence, wherein the modified amino acid sequence comprises a substitution of one or more epitope regions. The invention further relates to mutant genes encoding such variants and cleaning and personal care compositions comprising such variants.

12 Claims, No Drawings

FOREIGN PATENT DOCUMENTS

| | | |
|---|---|---|
| WO | WO 97/07770 | 3/1997 |
| WO | WO 97/24421 | 7/1997 |
| WO | WO 97/24427 | 7/1997 |
| WO | WO 97/30148 | 8/1997 |
| WO | WO 97/37007 | 10/1997 |
| WO | WO 98/23732 A2 | 6/1998 |
| WO | WO 98/30682 | 7/1998 |
| WO | WO 98/35026 | 8/1998 |
| WO | WO 99/00489 | 1/1999 |
| WO | WO 99/33868 A2 | 7/1999 |
| WO | WO 99/37324 A1 | 7/1999 |
| WO | WO 99/40936 A2 | 8/1999 |
| WO | WO 99/41369 A2 | 8/1999 |
| WO | WO 99/42097 A1 | 8/1999 |
| WO | WO 99/44635 A1 | 9/1999 |
| WO | WO 99/45904 A1 | 9/1999 |
| WO | WO 99/48918 A1 | 9/1999 |
| WO | WO 99/49056 A1 | 9/1999 |
| WO | WO 00/09707 A1 | 2/2000 |
| WO | WO 00/28007 A2 | 5/2000 |
| WO | WO 00/37658 A2 | 6/2000 |

OTHER PUBLICATIONS

Cui, J., et al., "Inhibition of T Helper Cell Type 2 Cell Differentiation and Immunoglobulin E Response by Ligand–activated Vα14 Natural Killer T Cells", J. Exp. Med., vol. 190, No. 6, pp. 783–792, (Sep. 20, 1999).

Deml, L., et al., "Immunostimulatory CpG Motifs Trigger a T Helper–1 Immune Response to Human Immunodeficiency Virus Type–1 (HIV–1) gp 160 Envelope Proteins", Clin Chem Lab Med, vol. 37, No. 3, pp. 199–204 (1999).

Ferru, I., et al., "Comparison of the Immune Response Elicited by a Free Peptide and a Lipopeptide Construct", Peptide Research, vol. 9, No. 3, pp. 136–143 (1996).

Haack, T., et al., "D–Amino Acids in Protein De Novo Design. II. Protein–diastereomerism Versus Protein–enantiomerism", Letters in Peptide Science, vol. 4, pp. 377–386 (1997).

Herve, M., et al., "On the Immunogenic Properties of Retro–Inverso Peptides. Total Retro–Inversion of T–Cell Epitopes Causes a Loss of Binding to MHC II Molecules", Molecular Immunology, vol. 34, No. 2, pp. 157–163 (1997).

Hoyne, G. F., et al., "Peptide–Mediated Regulation of the Allergic Immune Response", Immunology and Cell Biology, vol. 74, pp. 180–186 (1996).

Ikagawa, S., MD., et al., "Single Amino Acid Substitutions on a Japanese Cedar Pollen Alleren (Cry j 1)–derived Peptide Induced Alterations in Human T Cell Responses and T Cell Receptor Antagonism", J. Allergy Clin. Immuno, vol. 97, No. 1, Part 1, pp. 53–64 (Jan. 1996).

Lofthouse, S. A., et al., "Induction of $T_2$ (cytotoxic lymphocyte) and/or $T_1$ (antibody) Responses to a Mucin–1 Tumour Antigen", Vaccine, vol. 15, No. 14, pp. 1586–1593 (1997).

Maillere, B., et al., "Probing Immunogenicity of a T–Cell Epitope by L–Alanine and D–Amino Acid Scanning", Molecular Immunology, vol. 32, No. 14/15, pp. 1073–1080 (1995).

McKee, H. J., et al., "T Cell Cytokine Responses to Cartilage Aggrecan in BALB/c Mice", Biochemical Society Transactions, vol. 25, p311S (1997).

Moore, A., et al., "The Adjuvant Combination Monophosphoryl Lipid A and QS21 Switches T Cell Responses Induced With a Soluble Recombinant HIV Protein from Th2 and Th1", Vaccine, vol. 17, pp. 2517–2527 (1999).

Rosenthal, K.S., et al., "Immunization with a Leaps™ Heteroconjugate Containing a CTL Epitope and a Peptide from Beta–2–microglobulin Elicits a Protective and DTH Response to Herpes Simplex Virus Type 1", Vaccine, vol. 17, pp. 535–542 (1999).

Sinha, P., et al., "Minimized Fc Binding Peptide from Protein A Induces Immunocyte Proliferation and Evokes Th1–Type Response in Mice", Biochemical and Biophysical Research Communications, vol. 258, pp. 141–147 (1999).

Specht, C., et al., "The Murine (H–$2^K$) T–Cell Epitopes of Bee Venom Phospholipase $A_2$ Lie Outside the Active Site of the Enzyme", Int Arch Allergy Immunol, vol. 112, pp. 226–230 (1997).

Wiedermann, U., et al., "Effects of Adjuvants on the Immune Response to Allergens in a Murine Model of Allergen Inhalation: Cholera Toxin Induces a Th1–like Response to Bet V 1, the Major Birch Pollen Allergen", Clin Exp Immunol, vol. 111, pp. 144–151 (1998).

Zimmerman, D. H., et al., "Immunization with Peptide Heteroconjugates Primes a T Helper Cell Type 1–Associated Antibody (IgG2a) Response that Recognizes the Native Epitope on the 38–kDa Protein of *Mycobacterium tuberculosis*", Vaccine Research, vol. 5, No. 2, pp. 103–118 (1996).

Arlian, L.G. et al., "Antigenic and Allergenic Characteristics of the Enzyms Alcalase and Savinase by Crossed Immunoelectrophoresis and Crossed Radioimmunoelectrophoresis", Int. Arch Allergy Appl Immunol, vol. 91, pp. 278–284 (1990).

Abuchowski, A. et al., "Cancer Therapy with Chemically Modified Enzymes. I. Antitumor Properties of Polyethylene Glycol–Asparaginase Conjugates", Cancer Biochem Biophys, vol. 7, pp. 175–186 (1984).

Bungy Poor Fard, G.A. et al., T Cell Epitopes of the Major Fraction of Rye Grass Lolium Perenne (lol p I) Defined Using Overlapping Peptides in Vitro and In Vivo. I. Isoallergen Clone 1A, Clin Exp Immunol, vol. 94, pp. 111–116 (1993).

Caliceti, P. et al., "Active Site Protection of Proteolytic Enzymes by Poly(ethylene glycol) Surface Modification" Journal of Bioactive and Compatible Polymers, vol. 8, Jan., 1993, pp. 41–50.

Delgado, C. et al., "The Uses and Properties of PEG–Linked Proteins", Critical Review in Therapeutic Drug Carrier Systems, 9(3,4) (1992), pp. 249–304.

Favre, C. et al., "Epitope Mapping of Recombinant Human Gamma Interferon Using Monoclonal Antibodies", Molecular Immunology, vol. 26, No. 1, pp. 17–25 (1989).

Francis, G.E. et al., "PEG–Modified Proteins", Stability of Protein Pharmaceuticals, Part B: In Vivo Pathways of Degradation and Strategies for Protein Stabilization, edited by Ahern, T.J. and Mannin, M.C., Plenum Press (1992), pp. 235–263.

Hopp, T.P. et al., "Prediction of Protein Antigenic Determinants from Amino Acid Sequences", Proc. Natl Acad Sci, vol. 78, No. 6, pp. 3824–3828 (1981).

Katre, N.V., "The Conjugation of Proteins with Polyethylene Glycol and Other Polymers", Advanced Drug Delivery Reviews, 10(1993), pp. 92–114.

Khan, S.A. et al., "Polyethylene Glycol–modified Subtilisin Forms Microparticulate Suspensions in Organice Solvents", Enzyme Microb. Technology, vol. 14, Feb. (1992), pp. 96–100.

Masakatsu Ohta et al., "Preparation of a Dextran–Protease Conjugate and its Application to Cosmetic Use", 1996, Kanebo, Ltd., Cosmetics Laboratory, Japan, Cosmetics and Toiletries, vol. 111, pp. 79–88.

Monfardini, C. et al., "A Branched Monoethoxy Poly(ethylene glycol) for Protein Modification", Biconjugate Chemistry, vol. 6, No. 1 (1995), pp. 62–69.

Nishimura, H. et al., "Improved Modification of Yeast Uricase with Polyethylene Glycol, Accompanied with Non–immunoreactivity Towards Anti–Uricase Serum and High Enzymic Activity", Enzyme 26 (1981), pp. 49–53.

Nucci, M.L. et al., "The Therapeutic Value of Poly(ethylene glycol)–modified Proteins", Advanced Drug Delivery Reviews, 6 (1991), pp. 133–149.

Reay, P.A. et al., "Use of Global Amino Acid Replacements to Define the Requirements for MHC Binding and T Cell Recognition of Moth Cytochrome c(93–103)", Journal of Immunology, vol. 152, No. 8, pp. 3946–3957 (1994).

Ritz, H.L. et al., "Respiratory and Immunological Responses of Guinea Pigs to Enzyme–Containing Detergents: A Comparison of Intratracheal and Inhalation Modes of Exposure", Fundamental and Applied Toxicology, vol. 21, pp. 31–37 (1993).

Robinson, M.K., "Specific Antibody Responses to Subtilisin Carlsberg (Alcalase) in Mice: Development of an Intranasal Exposure Model", Fundamental and Applied Toxicology, vol. 24, pp. 15–24 (1996).

Savoca, K.V. et al., "Preparation of a Non–immunogenic Agrinase by the Covalent Attachment of Polyethylene Glycol", Biochemica Et Biophysica Acta, 578 (1979), pp. 47–53.

Siezen et al., "Homology Modelling and Protein Engineering Strategy of Subtilases, the Family of Subtilisin–Like Serine Proteases", Protein Engineering, vol. 4, No. 7, pp. 719–737 (1991).

Walsh, B.J. and M.E.H. Howden, "A Method for the Detection of IgE Binding Sequences of Allergens Based on a Modification of Epitope Mapping", Journal of Immunological Methods, vol. 121, pp. 275–280 (1989).

Mitchinson, C., et al., "Protein Engineering of Disulfide Bonds in Subtilisin BPN", Biochemistry, vol. 28, No. 11, pp. 4807–4815 (1989).

Nucci, M.L., et al., "Immunogenicity of Polyethylene Glycol–Modified Superoxide Dismutase and Catalase", J. Free Radicals in Biology & Medicine, vol. 2, pp. 321–325 (1986).

Gundlach, B.R., et al., "Determination of T Cell Epitopes with Random Peptide Libraries", Journal of Immunological Methods, vol. 192, pp. 149–155 (1996).

Siezen, R.J., et al., "Subtilases: The Superfamily of Subtilisin–like serine Proteases", Protein Science, vol. 6, No. 3, pp. 501–523 (1997).

Yang, M–L., et al., "Chemical Modification of Cobrotoxin with Bifuncitonal Reagent, 1,5–Difluor–2,4–Dinitrobenzene", Kaohsiung J. Med. Sci., vol. 4, pp. 503–513 (1988).

* cited by examiner

SEQUENCE LISTING

```
<160> NUMBER OF SEQ ID NOS:  1

<210> SEQ ID NO 1
<211> LENGTH: 275
<212> TYPE: PRT
<213> ORGANISM: Bacillus amyloliquefaciens

<400> SEQUENCE: 1

Ala Gln Ser Val Pro Tyr Gly Val Ser Gln Ile Lys Ala Pro Ala Leu
  1               5                  10                  15

His Ser Gln Gly Tyr Thr Gly Ser Asn Val Lys Val Ala Val Ile Asp
             20                  25                  30

Ser Gly Ile Asp Ser Ser His Pro Asp Leu Lys Val Ala Gly Gly Ala
         35                  40                  45

Ser Met Val Pro Ser Glu Thr Asn Pro Phe Gln Asp Asn Asn Ser His
     50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
```

-continued

```
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

SUBTILISIN PROTEASE VARIANTS HAVING AMINO ACID SUBSTITUTIONS IN DEFINED EPITOPE REGIONS

CROSS REFERENCE TO RELATED APPLICATION

This application claims the benefit of U.S. Provisional Application No. 60/144,980, filed Jul. 22, 1999.

FIELD OF THE INVENTION

The present invention relates to genetically engineered subtilisin proteases which are useful in compositions such as, for example, personal care compositions, laundry compositions, hard surface cleansing compositions, and light duty cleaning compositions.

BACKGROUND OF THE INVENTION

Enzymes make up the largest class of naturally occurring proteins. One class of enzyme includes proteases which catalyze the hydrolysis of other proteins. This ability to hydrolyze proteins has been exploited by incorporating naturally occurring and genetically engineered proteases into cleaning compositions, particularly those relevant to laundry applications.

In the cleaning arts, the mostly widely utilized of these proteases are the serine proteases.

Most of these serine proteases are produced by bacterial organisms while some are produced by other organisms, such as fungi. See Siezen, Roland J. et al., "Homology Modelling and Protein Engineering Strategy of Subtilases, the Family of Subtilisin-Like Serine Proteases", *Protein Engineering*, Vol. 4, No. 7, pp. 719–737 (1991). Unfortunately, the efficacy of the wild-type proteases in their natural environment is frequently not optimized for the artificial environment of a cleaning composition. Specifically, protease characteristics such as, for example, thermal stability, pH stability, oxidative stability and substrate specificity are not necessarily optimized for utilization outside the natural environment of the enzyme.

Several approaches have been employed to alter the wild-type amino acid sequence of serine proteases with the goal of increasing the efficacy of the protease in the unnatural wash environment. These approaches include the genetic redesign of proteases to enhance thermal stability and to improve oxidation stability under quite diverse conditions.

However, because such modified proteases are foreign to mammals, they are potential antigens. As antigens, these proteases cause an immunogenic and/or allergenic response (herein collectively described as immunogenic response) in mammals.

Furthermore, while genetic engineering has been prominent in the continuing search for more highly effective proteases for use in laundry applications, genetically engineered proteases have not been commercially utilized in personal care compositions and light duty detergents. A primary reason for the absence of engineered proteases in products such as, for example, soaps, gels, body washes, and shampoos, is due to the problem of human sensitization leading to undesirable immunological responses. It would therefore be highly advantageous to provide a personal care composition or light duty detergent which provides the cleansing properties of engineered proteases with minimized provocation of an immunological response.

One approach toward alleviating the immunological activity of a protease is through the redesign of one or more epitopes of the protease. Epitopes are those amino acid regions of an antigen which evoke an immunological response through the binding of antibodies or the presentation of processed antigens to T cells via a major histocompatibility complex protein (MHC). Changes in the epitopes can affect their efficiency as an antigen. See Walsh, B. J. and M. E. H. Howden, "A Method for the Detection of IgE Binding Sequences of Allergens Based on a Modification of Epitope Mapping", *Journal of Immunological Methods*, Vol. 121, pp. 275–280 (1989).

The present inventors have discovered that those serine proteases commonly known as subtilisins, including subtilisin BPN', have prominent epitope regions at amino acid positions 103–126 and 220–246, as well as at amino acid positions 70–84 corresponding to subtilisin BPN'. The present inventors have herein genetically redesigned such subtilisins to alleviate the immunogenic properties attributed to this epitope region. In so doing, the present inventors have discovered subtilisins which evoke a decreased immunological response yet maintain their activity as an efficient cleansing protease. Accordingly, the present proteases are suitable for use in several types of compositions including, but not limited to, laundry, dish, hard surface, skin care, hair care, beauty care, oral, and contact lens compositions.

SUMMARY OF THE INVENTION

The present invention relates to variants of serine proteases having decreased immunogenicity relative to their corresponding wild-type proteases. More particularly, the present invention relates to variants having a modified amino acid sequence of a wild-type amino acid sequence, wherein the modified amino acid sequence comprises a substitution of one or more epitope regions, wherein the epitope regions are 103–126 and 220–246 corresponding to subtilisin BPN'. Additionally, the present invention relates to modified amino acid sequences comprising one or more substitutions in two or more of epitope regions, wherein the epitope regions are 70–84, 103–126, and 220–246 corresponding to subtilisin BPN'. The invention further relates to mutant genes encoding such variants and cleaning and personal care compositions comprising such variants.

DETAILED DESCRIPTION OF THE INVENTION

The essential components of the present invention are herein described below. Also included are non-limiting descriptions of various optional and preferred components useful in embodiments of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, that may be present in commercially available sources.

All documents referred to herein, including all patents, patent applications, and printed publications, are hereby incorporated by reference in their entirety.

As used herein, abbreviations will be used to describe amino acids. Table I provides a list of abbreviations used herein:

TABLE I

| Amino Acid | Three-letter Abbreviation | One-letter Abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Definitions

As used herein, the term "mutation" refers to an alteration in a gene sequence and/or an amino acid sequence produced by those gene sequences. Mutations include deletions, substitutions, and additions of amino acid residues to the wild-type protein sequence.

As used herein, the term "wild-type" refers to a protein, herein specifically a protease, produced by unmutated organisms.

As used herein, the term "variant" means a protein, herein specifically a protease, having an amino acid sequence which differs from that of the corresponding wild-type protein.

As referred to herein, while the variants of the present invention are not limited to those of subtilisin BPN', all amino acid numbering is with reference to the amino acid sequence for subtilisin BPN' which is represented by SEQ ID NO:1. The amino acid sequence for subtilisin BPN' is further described by Wells et al., *Nucleic Acids Research*, Vol. 11, 7911–7925 (1983), incorporated herein by reference.

Variants of the Present Invention

The present inventors have discovered three epitope regions in serine proteases which correspond to positions 103–126 (referred to herein as the first epitope region), 220–246 (referred to herein as the second epitope region), and 70–84 (referred to herein as the third epitope region) of subtilisin BPN'. The present inventors have further discovered that one or more amino acid substitutions in one or more of the epitope regions provides variants which evoke a decreased allergenic and/or immune response relative to the corresponding wild-type serine protease.

As used herein, a variant may be designated by referring to the substituted amino acid positions which characterize the variant. Substitutions are herein indicated by providing the wild-type amino acid residue, followed by the position number, followed by the substituted amino acid residue to be substituted. Wherein the substituted amino acid residue may be any natural amino acid allowed at that particular position, the symbol "*" is provided. Multiple substitutions comprising a variant are separated by the symbol "+". To illustrate, a substitution of valine for glycine at position 70 is designated either Gly70Val or G70V. An example of a variant having a substitution at both positions 70 and 108 may be designated as Gly70Val+Ile108Ala or G70V+I108A.

The variants of the present invention are variants of subtilisin-like proteases. As used herein, the term "subtilisin-like protease" means a protease which has at least 50%, and preferably 80%, amino acid sequence identity with the sequences of subtilisin BPN'. Wild-type subtilisin-like proteases are produced by, for example, *Bacillus alcalophilus, Bacillus amyloliquefaciens, Bacillus amylosaccharicus, Bacillus licheniformis, Bacillus lentus*, and *Bacillus subtilis* microorganisms. A discussion relating to subtilisin-like serine proteases and their homologies may be found in Siezen et al., "Homology Modelling and Protein Engineering Strategy of Subtilases, the Family of Subtilisin-Like Serine Proteases", *Protein Engineering*, Vol. 4, No. 7, pp. 719–737 (1991).

The variants of the present invention are variants of serine proteases having a modified amino acid sequence of a wild-type amino acid sequence, wherein the modified amino acid sequence comprises a substitution by a substituting amino acid at one or more of positions in one or more epitope regions, wherein the first epitope region corresponds to positions 103, 104, 105, 106, 107, 108, 109, 110, 111, 112, 113, 114, 115, 116, 117, 118, 119, 120, 121, 122, 123, 124, 125, and 126 (103–126) of subtilisin BPN', and the second epitope region corresponds to positions 220, 221, 222, 223, 224, 225, 226, 227, 228, 229, 230, 231, 232, 233, 234, 235, 236, 237, 238, 239, 240, 241, 242, 243, 244, 245, and 246 (220–246) of subtilisin BPN'. More preferably, the modified amino acid sequence comprises a substitution at two or more of the foregoing positions. Even more preferably, the modified amino acid sequence comprises a substitution at three or more of the foregoing positions. Most preferably, the modified amino acid sequence comprises a substitution at four or more of the foregoing positions. Substitutions at these positions are made by replacing the wild-type amino acid residue with another natural amino acid residue such as one given in Table I.

Preferably, wherein the serine protease variant has a modified amino acid sequence of a wild-type amino acid sequence, the wild-type sequence comprising a first epitope region and a second epitope region, the modified amino acid sequence comprises a substitution by a substituting amino acid at one or more positions in one or more of the epitope regions, wherein:

(a) when a substitution occurs in the first epitope region, the substitution occurs at one or more of positions 103, 104, 105, 106, 107, 108, 109, 110, 111, 112, 113, 114, 115, 116, 117, 118, 119, 120, 121, 122, 123, 124, 125, and 126, wherein:

(i) when a substitution occurs at position 103, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr;

(ii) when a substitution occurs at position 104, the substituting amino acid is selected from the group consisting of Ala, Cys, Asp, Glu, Phe, Gly, His, Ile, Lys, Leu, Met, Asn, Pro, Gln, Arg, Ser, Thr, Val, and Trp;

(iii) when a substitution occurs at position 105, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(iv) when a substitution occurs at position 106, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(v) when a substitution occurs at position 107, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(vi) when a substitution occurs at position 108, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(vii) when a substitution occurs at position 109, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(viii) when a substitution occurs at position 110, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(ix) when a substitution occurs at position 110, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(x) when a substitution occurs at position 112, the substituting amino acid is selected from the group consisting of Ala, Cys, Asp, Phe, Gly, His, Ile, Lys, Leu, Met, Asn, Pro, Gln, Arg, Ser, Thr, Val, Trp, and Tyr;

(xi) when a substitution occurs at position 113, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(xii) when a substitution occurs at position 114, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiii) when a substitution occurs at position 115, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xiv) when a substitution occurs at position 116, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xv) when a substitution occurs at position 117, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xvi) when a substitution occurs at position 118, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xvii) when a substitution occurs at position 119, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(xviii) when a substitution occurs at position 120, the substituting amino acid is selected from the group consisting of Ala, Cys, Glu, Phe, Gly, His, Ile, Lys, Leu, Met, Asn, Pro, Gln, Arg, Ser, Thr, Val, Trp, and Tyr;

(xix) when a substitution occurs at position 121, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(xx) when a substitution occurs at position 122, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xxi) when a substitution occurs at position 123, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxii) when a substitution occurs at position 124, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(xxiii) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr; and (xxiv) when a substitution occurs at position 126, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr; and (b) when a substitution occurs in the second epitope region, the substitution occurs at one or more of positions 220, 221, 222, 223, 224, 225, 226, 227, 228, 229, 230, 231, 232, 233, 234, 235, 236, 237, 238, 239, 240, 241, 242, 243, 244, 245, and 246 wherein:

(i) when a substitution occurs at position 220, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(ii) when a substitution occurs at position 221, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(iii) when a substitution occurs at position 222, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(iv) when a substitution occurs at position 223, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(v) when a substitution occurs at position 224, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(vi) when a substitution occurs at position 225, the substituting amino acid is selected from the group consisting of Ala, Cys, Asp, Glu, Phe, Gly, His, Ile, Lys, Leu, Met, Asn, Gln, Arg, Ser, Thr, Val, Trp, and Tyr;

(vii) when a substitution occurs at position 226, the substituting amino acid is selected from the group consisting of Ala, Cys, Asp, Glu, Phe, Gly, Ile, Lys, Leu, Met, Asn, Pro, Gln, Arg, Ser, Thr, Val, Trp, and Tyr;

(viii) when a substitution occurs at position 227, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(ix) when a substitution occurs at position 228, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(x) when a substitution occurs at position 229, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(xi) when a substitution occurs at position 230, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xii) when a substitution occurs at position 231, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiii) when a substitution occurs at position 232, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiv) when a substitution occurs at position 233, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xv) when a substitution occurs at position 234, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xvi) when a substitution occurs at position 235, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xvii) when a substitution occurs at position 236, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(xviii) when a substitution occurs at position 237, the substituting amino acid is selected from the group consisting of Ala, Cys, Asp, Glu, Phe, Gly, His, Ile, Leu, Met, Asn, Pro, Gln, Arg, Ser, Thr, Val, Trp, and Tyr;

(xix) when a substitution occurs at position 238, the substituting amino acid is selected from the group consisting of Ala, Cys, Asp, Glu, Phe, Gly, Ile, Lys, Leu, Met, Asn, Pro, Gln, Arg, Ser, Thr, Val, Trp, and Tyr;

(xx) when a substitution occurs at position 239, the substituting amino acid is selected from the group consisting of Ala, Cys, Asp, Glu, Phe, Gly, His, Ile, Lys, Leu, Met, Asn, Gln, Arg, Ser, Thr, Val, Trp, and Tyr;

(xxi) when a substitution occurs at position 240, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxii) when a substitution occurs at position 241, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(xxiii) when a substitution occurs at position 242, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxiv) when a substitution occurs at position 243, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxv) when a substitution occurs at position 244, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxvi) when a substitution occurs at position 245, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr; and (xxvii) when a substitution occurs at position 246, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr.

More preferably, wherein the serine protease variant has a modified amino acid sequence of a wild-type amino acid sequence, the wild-type sequence comprising a first epitope region and a second epitope region, the modified amino acid sequence comprises a substitution by a substituting amino acid at one or more positions in one or more of the epitope regions, wherein:

(a) when a substitution occurs in the first epitope region, the substitution occurs at one or more of positions 108, 109, 110, 111, 112, 113, 114, 115, 116, 117, 118, 119, 120, 121, 122, 123, 124, 125, and 126, wherein:

(i) when a substitution occurs at position 108, the substituting amino acid is selected from the group consisting of Ala, Cys, Asp, Glu, Phe, Gly, His, Lys, Leu, Met, Asn, Pro, Gln, Arg, Ser, Thr, Trp, and Tyr;

(ii) when a substitution occurs at position 109, the substituting amino acid is selected from the group consisting of Ala, Phe, Gly, His, Leu, Met, Pro, Gln, Trp, and Tyr;

(iii) when a substitution occurs at position 110, the substituting amino acid is selected from the group consisting of Ala, Asp, Glu, Phe, His, Ile, Lys, Leu, Met, Asn, Pro, Gln, Ser, Thr, Val, Trp, and Tyr;

(iv) when a substitution occurs at position 111, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(v) when a substitution occurs at position 112, the substituting amino acid is selected from the group consisting of Ala, Cys, Asp, Phe, Gly, His, Ile, Lys, Leu, Met, Asn, Pro, Gln, Arg, Ser, Val, Trp, and Tyr;

(vi)when a substitution occurs at position 113, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(vii) when a substitution occurs at position 114, the substituting amino acid is selected from the group consisting of Asp, Glu, Phe, Gly, His, Ile, Lys, Leu, Met, Asn, Pro, Gln, Arg, Ser, Thr, Val, Trp, and Tyr;

(viii) when a substitution occurs at position 115, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(ix) when a substitution occurs at position 116, the substituting amino acid is selected from the group consisting of Cys, Asp, Phe, Gly, His, Ile, Leu, Met, Asn, Pro, Gln, Ser, Val, Trp, and Tyr;

(x) when a substitution occurs at position 117, the substituting amino acid is selected from the group consisting of Ala, Cys, Asp, Glu, Phe, Gly, His, Ile, Leu, Met, Pro, Gln, Ser, Thr, Val, Trp, and Tyr;

(xi) when a substitution occurs at position 118, the substituting amino acid is selected from the group consisting of Cys, Asp, Glu, Phe, Gly, His, Lys, Met, Gln, Arg, Thr, Trp, and Tyr;

(xii) when a substitution occurs at position 119, the substituting amino acid is selected from the group consisting of Ala, Asp, Glu, Phe, Gly, His, Ile, Lys, Leu, Asn, Pro, Gln, Arg, Ser, Thr, Val, Trp, and Tyr;

(xiii) when a substitution occurs at position 120, the substituting amino acid is selected from the group consisting of Ala, Cys, Glu, Phe, Gly, Ile, Leu, Met, Pro, Gln, Arg, Ser, Thr, Val, Trp, and Tyr;

(xiv) when a substitution occurs at position 121, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(xv) when a substitution occurs at position 122, the substituting amino acid is selected from the group consisting of Ala, Asp, Glu, Phe, Gly, His, Lys, Leu, Met, Asn, Pro, Gln, Arg, Ser, Thr, Val, Trp, and Tyr;

(xvi) when a substitution occurs at position 123, the substituting amino acid is selected from the group consisting of Asp, Glu, Phe, His, Lys, Leu, Met, Pro, Gln, Arg, Val, Trp, and Tyr;

(xvii) when a substitution occurs at position 124, the substituting amino acid is selected from the group consisting of Cys, Asp, Glu, Phe, Gly, His, Asn, Pro, Gln, Arg, Ser, Thr, Val, Trp, and Tyr;

(xviii) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr; and (xix) when a substitution occurs at position 126, the substituting amino acid is selected from the group consisting of Ala, Cys, Asp, Glu, Phe, Gly, His, Lys, Met, Asn, Pro, Gln, Arg, Ser, Thr, Val, Trp, and Tyr; and (b) when a substitution occurs in the second epitope region, the substitution occurs at one or more of positions 221, 223, 224, 225, 226, 227, 228, 229, 230, 231, 232, 233, 234, 235, 236, 237, 238, 239, 240, 241, 242, 243, 244, 245, and 246 wherein:

(i) when a substitution occurs at position 221, the substituting amino acid is selected from the group consisting of Asp, Glu, Phe, Gly, His, Ile, Lys, Leu, Met, Asn, Pro, Gln, Arg, Thr, Val, Trp, and Tyr;

(ii) when a substitution occurs at position 223, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(iii) when a substitution occurs at position 224, the substituting amino acid is selected from the group consisting of Ala, Asp, Glu, Phe, Gly, His, Ile, Lys, Leu, Met, Asn, Pro, Gln, Arg, Val, Trp, and Tyr;

(iv) when a substitution occurs at position 225, the substituting amino acid is selected from the group consisting of Cys, Asp, Phe, Gly, His, Ile, Asn, Thr, Trp, and Tyr;

(v) when a substitution occurs at position 226, the substituting amino acid is selected from the group consisting of Ala, Asp, Glu, Phe, Gly, Ile, Lys, Leu, Met, Asn, Pro, Gln, Arg, Thr, Val, Trp, and Tyr;

(vi) when a substitution occurs at position 227, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(vii) when a substitution occurs at position 228, the substituting amino acid is selected from the group consisting of Asp, Glu, Phe, Gly, His, Ile, Lys, Leu, Met, Asn, Pro, Gln, Arg, Ser, Thr, Val, Trp, and Tyr;

(viii) when a substitution occurs at position 229, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(ix) when a substitution occurs at position 230, the substituting amino acid is selected from the group consisting of Asp, Glu, Phe, Gly, His, Ile, Lys, Leu, Met, Asn, Pro, Gln, Arg, Ser, Thr, Val, Trp, and Tyr;

(x) when a substitution occurs at position 231, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xi) when a substitution occurs at position 232, the substituting amino acid is selected from the group consisting of Asp, Glu, Phe, Gly, His, Ile, Lys, Leu, Met, Asn, Pro, Gln, Arg, Ser, Thr, Val, Trp, and Tyr;

(xii) when a substitution occurs at position 233, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xiii) when a substitution occurs at position 234, the substituting amino acid is selected from the group consisting of Ala, Asp, Glu, Phe, Gly, His, Lys, Leu, Met, Asn, Pro, Gln, Arg, Ser, Thr, Val, Trp, and Tyr;

(xiv) when a substitution occurs at position 235, the substituting amino acid is selected from the group consisting of Ala, Asp, Glu, Phe, Gly, His, Ile, Met, Asn, Pro, Gln, Ser, Thr, Val, Trp, and Tyr;

(xv) when a substitution occurs at position 236, the substituting amino acid is selected from the group consisting of Ala, Asp, Glu, Phe, Gly, His, Ile, Lys, Leu, Met, Asn, Pro, Gln, Arg, Thr, Val, Trp, and Tyr;

(xvi) when a substitution occurs at position 237, the substituting amino acid is selected from the group consisting of Ala, Cys, Asp, Glu, Phe, Gly, His, Ile, Leu, Met, Asn, Pro, Gln, Ser, Thr, Val, Trp, and Tyr;

(xvii) when a substitution occurs at position 238, the substituting amino acid is selected from the group consisting of Ala, Asp, Glu, Phe, Gly, Ile, Lys, Leu, Met, Asn, Pro, Gln, Arg, Ser, Thr, Val, Trp, and Tyr;

(xviii) when a substitution occurs at position 239, the substituting amino acid is selected from the group consisting of Ala, Cys, Asp, Glu, Phe, Gly, His, Ile, Lys, Leu, Met, Asn, Gln, Arg, Ser, Thr, Val, Trp, and Tyr;

(xix) when a substitution occurs at position 240, the substituting amino acid is selected from the group consisting of Ala, Cys, Asp, Glu, Phe, Gly, His, Ile, Leu, Met, Pro, Gln, Ser, Thr, Val, Trp, and Tyr;

(xx) when a substitution occurs at position 241, the substituting amino acid is selected from the group consisting of Ala, Cys, Asp, Glu, Phe, Gly, His, Ile, Lys, Met, Asn, Gln, Arg, Ser, Thr, and Val;

(xxi) when a substitution occurs at position 242, the substituting amino acid is selected from the group consisting of Ala, Cys, Asp, Glu, Phe, Gly, His, Ile, Lys, Leu, Met, Asn, Gln, Arg, Ser, Val, Trp, and Tyr;

(xxii) when a substitution occurs at position 243, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxiii) when a substitution occurs at position 244, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxiv) when a substitution occurs at position 245, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr; and (xxv) when a substitution occurs at position 246, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr.

Even more preferably, wherein the serine protease variant has a modified amino acid sequence of a wild-type amino acid sequence, the wild-type sequence comprising a first epitope region and a second epitope region, the modified amino acid sequence comprises a substitution by a substituting amino acid at two or more positions in one or more of the epitope regions, wherein:

(a) when a substitution occurs in the first epitope region, the substitution occurs at one or more of positions 108, 109, 110, 111, 112, 113, 114, 115, 116, 117, 118, 119, 120, 121, 122, 123, 124, and 125 wherein:

(i) when a substitution occurs at position 108, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(ii) when a substitution occurs at position 109, the substituting amino acid is selected from the group consisting of Ala, Cys, Asp, Glu, Phe, Gly, His, Ile, Lys, Leu, Met, Pro, Gln, Arg, Thr, Val, Trp, and Tyr;

(iii) when a substitution occurs at position 110, the substituting amino acid is selected from the group consisting of Ala, Cys, Asp, Glu, Phe, Ile, Lys, Leu, Met, Asn, Pro, Gln, Arg, Ser, Thr, Val, Trp, and Tyr;

(iv) when a substitution occurs at position 111, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(v) when a substitution occurs at position 112, the substituting amino acid is selected from the group consisting of Ala, Cys, Asp, Phe, Gly, His, Ile, Lys, Leu, Met, Asn, Pro, Gln, Arg, Ser, Thr, Val, Trp, and Tyr;

(vi) when a substitution occurs at position 113, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(vii) when a substitution occurs at position 114, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(viii) when a substitution occurs at position 115, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(ix) when a substitution occurs at position 116, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(x) when a substitution occurs at position 117, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xi) when a substitution occurs at position 118, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xii) when a substitution occurs at position 119, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(xiii) when a substitution occurs at position 120, the substituting amino acid is selected from the group consisting of Ala, Cys, Glu, Phe, Gly, Ile, Lys, Leu, Met, Asn, Pro, Gln, Arg, Ser, Thr, Val, Trp, and Tyr;

(xiv) when a substitution occurs at position 121, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(xv) when a substitution occurs at position 122, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xvi) when a substitution occurs at position 123, the substituting amino acid is selected from the group consisting of Ala, Asp, Glu, Phe, Gly, His, Ile, Lys, Leu, Met, Pro, Gln, Arg, Ser, Thr, Val, Trp, and Tyr;

(xvii) when a substitution occurs at position 124, the substituting amino acid is selected from the group consisting of Cys, Asp, Glu, Phe, Gly, His, Lys, Asn, Pro, Gln, Arg, Ser, Thr, Val, Trp, and Tyr; and (xviii) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr; and (b) when a substitution occurs in the second epitope region, the substitution occurs at one or more of positions 221, 222, 223, 224, 225, 226, 227, 228, 229, 230, 231, 232, 233, 234, 235, 236, 237, 238, 239, 240, 241, 242, 243, 244, 245, and 246 wherein:

(i) when a substitution occurs at position 221, the substituting amino acid is selected from the group consisting of Ala, Asp, Glu, Phe, Gly, His, Ile, Lys, Leu, Met, Asn, Pro, Gln, Arg, Thr, Val, Trp, and Tyr;

(ii) when a substitution occurs at position 222, the substituting amino acid is selected from the group consisting of Cys, Asp, Glu, Phe, Gly, His, Ile, Lys, Asn, Pro, Arg, Ser, Thr, Val, Trp, and Tyr;

(iii) when a substitution occurs at position 223, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(iv) when a substitution occurs at position 224, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(v) when a substitution occurs at position 225, the substituting amino acid is selected from the group consisting of Cys, Asp, Glu, Phe, Gly, His, Ile, Lys, Leu, Met, Asn, Gln, Arg, Ser, Thr, Val, Trp, and Tyr;

(vi) when a substitution occurs at position 226, the substituting amino acid is selected from the group consisting of Ala, Cys, Asp, Glu, Phe, Gly, Ile, Lys, Leu, Met, Asn, Pro, Gln, Arg, Thr, Val, Trp, and Tyr;

(vii) when a substitution occurs at position 227, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(viii) when a substitution occurs at position 228, the substituting amino acid is selected from the group consisting of Asp, Glu, Phe, Gly, His, Ile, Lys, Leu, Met, Asn, Pro, Gln, Arg, Ser, Thr, Val, Trp, and Tyr;

(ix) when a substitution occurs at position 229, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(x) when a substitution occurs at position 230, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xi) when a substitution occurs at position 231, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xii) when a substitution occurs at position 232, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiii) when a substitution occurs at position 233, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xiv) when a substitution occurs at position 234, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xv) when a substitution occurs at position 235, the substituting amino acid is selected from the group consisting of Ala, Cys, Asp, Glu, Phe, Gly, His, Ile, Lys, Met, Asn, Pro, Gln, Ser, Thr, Val, Trp, and Tyr;

(xvi) when a substitution occurs at position 236, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(xvii) when a substitution occurs at position 237, the substituting amino acid is selected from the group consisting of Ala, Cys, Asp, Glu, Phe, Gly, His, Ile, Met, Asn, Pro, Gln, Ser, Thr, Val, Trp, and Tyr;

(xviii) when a substitution occurs at position 238, the substituting amino acid is selected from the group consisting of Ala, Cys, Asp, Glu, Phe, Gly, Ile, Lys, Leu, Met, Asn, Pro, Gln, Arg, Ser, Thr, Val, Trp, and Tyr;

(xix) when a substitution occurs at position 239, the substituting amino acid is selected from the group consisting of Ala, Asp, Glu, Phe, Gly, His, Ile, Lys, Leu, Met, Asn, Gln, Arg, Ser, Thr, Val, Trp, and Tyr;

(xx) when a substitution occurs at position 240, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxi) when a substitution occurs at position 241, the substituting amino acid is selected from the group consisting of Ala, Asp, Glu, Phe, Gly, His, Ile, Lys, Leu, Met, Asn, Gln, Arg, Ser, Thr, Val, and Tyr;

(xxii) when a substitution occurs at position 242, the substituting amino acid is selected from the group consisting of Ala, Cys, Asp, Glu, Phe, Gly, His, Ile, Lys, Leu, Met, Asn, Gln, Arg, Ser, Val, Trp, and Tyr;

(xxiii) when a substitution occurs at position 243, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxiv) when a substitution occurs at position 244, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxv) when a substitution occurs at position 245, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr; and (xxvi) when a substitution occurs at position 246, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr.

In another preferred embodiment of the present invention, the variants comprise a substitution by a substituting amino acid at one or more positions in two or more epitope regions. In this embodiment, the epitope regions are a first epitope region corresponding to positions 103–126 of subtilisin BPN', a second epitope region corresponding to positions 220–246 of subtilisin BPN', and a third epitope region corresponding to positions 70, 71, 72, 73, 74, 75, 76, 77, 78, 79, 80, 81, 82, 83, and 84 (70–84) of subtilisin BPN'. In this embodiment, the phrase "a substitution by a substituting amino acid at one or more positions in two or more epitope regions" means that at least one substitution occurs in one of the epitope regions and at least one substitution occurs in a different epitope region. Of course, in this embodiment, at least one substitution can occur in each of the epitope regions. Preferably in this embodiment, the modified amino acid sequence comprises a substitution by a substituting amino acid at two or more positions in one or more of the epitope regions (i.e., the variant comprises a substitution by a substituting amino acid at one or more positions in one or more of the epitope regions and a substitution by a substituting amino acid at two or more positions in another epitope region). More preferably in this embodiment, the modified amino acid sequence comprises a substitution by a substituting amino acid at three or more positions in one or more of the epitope regions (i.e., the variant comprises a substitution by a substituting amino acid at one or more positions in one or more of the epitope regions and a substitution by a substituting amino acid at three or more positions in another epitope region). Substitutions at the foregoing positions are made by replacing the wild-type amino acid residue with another natural amino acid residue such as one given in Table I.

Preferably in this embodiment, the serine protease variant has a modified amino acid sequence of a wild-type amino acid sequence, the wild-type sequence comprising a first epitope region, a second epitope region, and a third epitope region, wherein the modified amino acid sequence comprises a substitution by a substituting amino acid at one or more positions in two or more of the epitope regions, wherein:

(a) when a substitution occurs in the first epitope region, the substitution occurs at one or more of positions 103, 104, 105, 106, 107, 108, 109, 110, 111, 112, 113, 114, 115, 116, 117, 118, 119, 120, 121, 122, 123, 124, 125, and 126, wherein:
 (i) when a substitution occurs at position 103, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr;
 (ii) when a substitution occurs at position 104, the substituting amino acid is selected from the group consisting of Ala, Cys, Asp, Glu, Phe, Gly, His, Ile, Lys, Leu, Met, Asn, Pro, Gln, Arg, Ser, Thr, Val, and Trp;
 (iii) when a substitution occurs at position 105, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;
 (iv) when a substitution occurs at position 106, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;
 (v) when a substitution occurs at position 107, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;
 (vi) when a substitution occurs at position 108, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;
 (vii) when a substitution occurs at position 109, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;
 (viii) when a substitution occurs at position 110, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;
 (ix) when a substitution occurs at position 111, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;
 (x) when a substitution occurs at position 112, the substituting amino acid is selected from the group consisting of Ala, Cys, Asp, Phe, Gly, His, Ile, Lys, Leu, Met, Asn, Pro, Gln, Arg, Ser, Thr, Val, Trp, and Tyr;
 (xi) when a substitution occurs at position 113, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;
 (xii) when a substitution occurs at position 114, the substituting amino acid is selected from the group consisting of Cys, Asp,.Glu, Phe, Gly, His, Ile, Lys, Leu, Met, Asn, Pro, Gln, Arg, Ser, Thr, Val, Trp, and Tyr;
 (xiii) when a substitution occurs at position 115, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;
 (xiv) when a substitution occurs at position 116, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;
 (xv) when a substitution occurs at position 117, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;
 (xvi) when a substitution occurs at position 118, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;
 (xvii) when a substitution occurs at position 119, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;
 (xviii) when a substitution occurs at position 120, the substituting amino acid is selected from the group consisting of Ala, Cys, Glu, Phe, Gly, His, Ile, Lys, Leu, Met, Asn, Pro, Gln, Arg, Ser, Thr, Val, Trp, and Tyr;
 (xix) when a substitution occurs at position 121, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(xx) when a substitution occurs at position 122, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xxi) when a substitution occurs at position 123, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxii) when a substitution occurs at position 124, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(xxiii) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr; and (xxiv) when a substitution occurs at position 126, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr; and (b) when a substitution occurs in the second epitope region, the substitution occurs at one or more of positions 220, 221, 222, 223, 224, 225, 226, 227, 228, 229, 230, 231, 232, 233, 234, 235, 236, 237, 238, 239, 240, 241, 242, 243, 244, 245, and 246 wherein:

(i) when a substitution occurs at position 220, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(ii) when a substitution occurs at position 221, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(iii) when a substitution occurs at position 222, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(iv) when a substitution occurs at position 223, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(v) when a substitution occurs at position 224, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(vi) when a substitution occurs at position 225, the substituting amino acid is selected from the group consisting of Ala, Cys, Asp, Glu, Phe, Gly, His, Ile, Lys, Leu, Met, Asn, Gln, Arg, Ser, Thr, Val, Trp, and Tyr;

(vii) when a substitution occurs at position 226, the substituting amino acid is selected from the group consisting of Ala, Cys, Asp, Glu, Phe, Gly, Ile, Lys, Leu, Met, Asn, Pro, Gln, Arg, Ser, Thr, Val, Trp, and Tyr;

(viii) when a substitution occurs at position 227, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(ix) when a substitution occurs at position 228, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(x) when a substitution occurs at position 229, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(xi) when a substitution occurs at position 230, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xii) when a substitution occurs at position 231, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiii) when a substitution occurs at position 232, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiv) when a substitution occurs at position 233, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xv) when a substitution occurs at position 234, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xvi) when a substitution occurs at position 235, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xvii) when a substitution occurs at position 236, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(xviii) when a substitution occurs at position 237, the substituting amino acid is selected from the group consisting of Ala, Cys, Asp, Glu, Phe, Gly, His, Ile, Leu, Met, Asn, Pro, Gln, Arg, Ser, Thr, Val, Trp, and Tyr;

(xix) when a substitution occurs at position 238, the substituting amino acid is selected from the group consisting of Ala, Cys, Asp, Glu, Phe, Gly, Ile, Lys, Leu, Met, Asn, Pro, Gln, Arg, Ser, Thr, Val, Trp, and Tyr;

(xx) when a substitution occurs at position 239, the substituting amino acid is selected from the group consisting of Ala, Cys, Asp, Glu, Phe, Gly, His, Ile, Lys, Leu, Met, Asn, Gln, Arg, Ser, Thr, Val, Trp, and Tyr;

(xxi) when a substitution occurs at position 240, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxii) when a substitution occurs at position 241, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(xxiii) when a substitution occurs at position 242, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxiv) when a substitution occurs at position 243, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxv) when a substitution occurs at position 244, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxvi) when a substitution occurs at position 245, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr; and (xxvii) when a substitution occurs at position 246, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr; and (c) when a substitution occurs in the third epitope region, the substitution occurs at one or more of positions 70, 71, 72, 73, 74, 75, 76, 77, 78, 79, 80, 81, 82, 83, and 84 wherein:

(i) when a substitution occurs at position 70, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(ii) when a substitution occurs at position 71, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(iii) when a substitution occurs at position 72, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(iv) when a substitution occurs at position 73, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(v) when a substitution occurs at position 74, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(vi) when a substitution occurs at position 75, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(vii) when a substitution occurs at position 76, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(viii) when a substitution occurs at position 77, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(ix) when a substitution occurs at position 78, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(x) when a substitution occurs at position 79, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xi) when a substitution occurs at position 80, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(xii) when a substitution occurs at position 81, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(xiii) when a substitution occurs at position 82, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xiv) when a substitution occurs at position 83, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr; and (xv) when a substitution occurs at position 84, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr.

More preferably in this embodiment, the serine protease variant has a modified amino acid sequence of a wild-type amino acid sequence, the wild-type sequence comprising a first epitope region, a second epitope region, and a third epitope region, wherein the modified amino acid sequence comprises a substitution by a substituting amino acid at one or more positions in two or more of the epitope regions, wherein:

(a) when a substitution occurs in the first epitope region, the substitution occurs at one or more of positions 108, 109, 110, 111, 112, 113, 114, 115, 116, 117, 118, 119, 120, 121, 122, 123, 124, and 125 wherein:

(i) when a substitution occurs at position 108, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(ii) when a substitution occurs at position 109, the substituting amino acid is selected from the group consisting of Ala, Cys, Asp, Glu, Phe, Gly, His, Ile, Lys, Leu, Met, Pro, Gln, Arg, Thr, Val, Trp, and Tyr;

(iii) when a substitution occurs at position 110, the substituting amino acid is selected from the group consisting of Ala, Cys, Asp, Glu, Phe, Ile, Lys, Leu, Met, Asn, Pro, Gln, Arg, Ser, Thr, Val, Trp, and Tyr;

(iv) when a substitution occurs at position 111, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(v) when a substitution occurs at position 112, the substituting amino acid is selected from the group consisting of Ala, Cys, Asp, Phe, Gly, His, Ile, Lys, Leu, Met, Asn, Pro, Gln, Arg, Ser, Thr, Val, Trp, and Tyr;

(vi) when a substitution occurs at position 113, the substituting amino acid is selected from the group consisting of Ala, Cys, Asp, Glu, Phe, Gly, His, Ile, Lys, Leu, Met, Asn, Pro, Gln, Arg, Ser, Thr, Val, and Tyr;

(vii) when a substitution occurs at position 114, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(viii) when a substitution occurs at position 115, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(ix) when a substitution occurs at position 116, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(x) when a substitution occurs at position 117, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xi) when a substitution occurs at position 118, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xii) when a substitution occurs at position 119, the substituting amino acid is selected from the group consisting of Ala, Cys, Asp, Glu, Phe, Gly, His, Ile, Lys, Leu, Asn, Pro, Gln, Arg, Ser, Thr, Val, Trp, and Tyr;

(xiii) when a substitution occurs at position 120, the substituting amino acid is selected from the group consisting of Ala, Cys, Glu, Phe, Gly, Ile, Leu, Met, Asn, Pro, Gln, Arg, Ser, Thr, Val, Trp, and Tyr;

(xiv) when a substitution occurs at position 121, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(xv) when a substitution occurs at position 122, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xvi) when a substitution occurs at position 123, the substituting amino acid is selected from the group consisting of Ala, Asp, Glu, Phe, Gly, His, Ile, Lys, Leu, Met, Pro, Gln, Arg, Thr, Val, Trp, and Tyr;

(xvii) when a substitution occurs at position 124, the substituting amino acid is selected from the group consisting of Cys, Asp, Glu, Phe, Gly, His, Lys, Asn, Pro, Gln, Arg, Ser, Thr, Val, Trp, and Tyr; and (xviii) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(b) when a substitution occurs in the second epitope region, the substitution occurs at one or more of positions 221, 222, 223, 224, 225, 226, 227, 228, 229, 230, 231, 232, 233, 234, 235, 236, 237, 238, 239, 240, 241, 242, 243, 244, 245, and 246 wherein:

(i) when a substitution occurs at position 221, the substituting amino acid is selected from the group consisting of Ala, Asp, Glu, Phe, Gly, His, Ile, Lys, Leu, Met, Asn, Pro, Gln, Arg, Thr, Val, Trp, and Tyr;

(ii) when a substitution occurs at position 222, the substituting amino acid is selected from the group consisting of Cys, Asp, Glu, Phe, Gly, His, Ile, Lys, Asn, Pro, Arg, Ser, Thr, Val, Trp, and Tyr;

(iii) when a substitution occurs at position 223, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(iv) when a substitution occurs at position 224, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(v) when a substitution occurs at position 225, the substituting amino acid is selected from the group consisting of Cys, Asp, Glu, Phe, Gly, His, Ile, Lys, Leu, Met, Asn, Gln, Arg, Ser, Thr, Val, Trp, and Tyr;

(vi) when a substitution occurs at position 226, the substituting amino acid is selected from the group consisting of Ala, Cys, Asp, Glu, Phe, Gly, Ile, Lys, Leu, Met, Asn, Pro, Gln, Arg, Thr, Val, Trp, and Tyr;

(vii) when a substitution occurs at position 227, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr;

(viii) when a substitution occurs at position 228, the substituting amino acid is selected from the group consisting of Asp, Glu, Phe, Gly, His, Ile, Lys, Leu, Met, Asn, Pro, Gln, Arg, Ser, Thr, Val, Trp, and Tyr;

(ix) when a substitution occurs at position 229, the substituting amino acid is selected from the group consisting of Ala, Cys, Asp, Glu, Phe, His, Ile, Lys, Leu, Met, Asn, Pro, Gln, Arg, Ser, Thr, Val, Trp, and Tyr;

(x) when a substitution occurs at position 230, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xi) when a substitution occurs at position 231, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xii) when a substitution occurs at position 232, the substituting amino acid is selected from the group consisting of Cys, Asp, Glu, Phe, Gly, His, Ile, Lys, Leu, Met, Asn, Pro, Gln, Arg, Ser, Thr, Val, Trp, and Tyr;

(xiii) when a substitution occurs at position 233, the substituting amino acid is selected from the group consisting of Ala, Cys, Asp, Glu, Phe, Gly, His, Ile, Lys, Met, Asn, Pro, Gln, Arg, Ser, Thr, Val, Trp, and Tyr;

(xiv) when a substitution occurs at position 234, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(xv) when a substitution occurs at position 235, the substituting amino acid is selected from the group consisting of Ala, Cys, Asp, Glu, Phe, Gly, His, Ile, Lys, Met, Asn, Pro, Gln, Ser, Thr, Val, Trp, and Tyr;

(xvi) when a substitution occurs at position 236, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr;

(xvii) when a substitution occurs at position 237, the substituting amino acid is selected from the group consisting of Ala, Cys, Asp, Glu, Phe, Gly, His, Ile, Met, Asn, Pro, Gln, Ser, Thr, Val, Trp, and Tyr;

(xviii) when a substitution occurs at position 238, the substituting amino acid is selected from the group consisting of Ala, Cys, Asp, Glu, Phe, Gly, Ile, Lys, Leu, Met, Asn, Pro, Gln, Arg, Ser, Thr, Val, Trp, and Tyr;

(xix) when a substitution occurs at position 239, the substituting amino acid is selected from the group consisting of Ala, Asp, Glu, Phe, Gly, His, Ile, Lys, Leu, Met, Asn, Gln, Arg, Ser, Thr, Val, Trp, and Tyr;

(xx) when a substitution occurs at position 240, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxi) when a substitution occurs at position 241, the substituting amino acid is selected from the group consisting of Ala, Asp, Glu, Phe, Gly, His, Ile, Lys, Leu, Met, Asn, Gln, Arg, Ser, Thr, Val, and Tyr;

(xxii) when a substitution occurs at position 242, the substituting amino acid is selected from the group consisting of Ala, Cys, Asp, Glu, Phe, Gly, His, Ile, Lys, Leu, Met, Asn, Gln, Arg, Ser, Val, Trp, and Tyr;

(xxiii) when a substitution occurs at position 243, the substituting amino acid is selected from the group consisting of Ala, Cys, Asp, Glu, Phe, Gly, His, Ile, Lys, Leu, Met, Pro, Gln, Arg, Ser, Thr, Val, Trp, and Tyr;

(xxiv) when a substitution occurs at position 244, the substituting amino acid is selected from the group consisting of Ala, Cys, Asp, Glu, Phe, Gly, His, Ile, Lys, Leu, Met, Asn, Pro, Gln, Arg, Ser, Val, Trp, and Tyr;

(xxv) when a substitution occurs at position 245, the substituting amino acid is selected from the group consisting of Ala, Cys, Asp, Glu, Phe, Gly, His, Ile, Lys, Leu, Met, Asn, Pro, Arg, Ser, Thr, Val, Trp, and Tyr; and (xxvi) when a substitution occurs at position 246, the substituting amino acid is selected from the group consisting of Ala, Cys, Asp, Glu, Phe, Gly, His, Ile, Lys, Leu, Met, Asn, Pro, Gln, Arg, Ser, Thr, Trp, and Tyr; and (c) when a substitution occurs in the second epitope region, the substitution occurs at one or more of positions 70, 71, 72, 73, 74, 75, 76, 77, 78, 79, 80, 81, 82, 83, and 84 wherein:

(i) when a substitution occurs at position 70, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val;

(ii) when a substitution occurs at position 71, the substituting amino acid is selected from the group consisting of Ala, Arg, Asn, Asp, Cys, Gln, Glu, Gly, Phe, His, Ile, Lys, Leu, Met, Pro, Ser, Trp, Tyr, and Val;

(iii) when a substitution occurs at position 72, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr;

(iv) when a substitution occurs at position 73, the substituting amino acid is selected from the group consisting of Arg, Asn, Asp, Cys, Gln, Glu, Gly, Phe, His, Ile, Lys, Leu, Met, Pro, Ser, Thr, Trp, Tyr, and Val;

(v) when a substitution occurs at position 74, the substituting amino acid is selected from the group consisting of Arg, Asn, Asp, Cys, Gln, Glu, Gly, Phe, His, Ile, Lys, Leu, Met, Pro, Ser, Thr, Trp, Tyr, and Val;

(vi) when a substitution occurs at position 75, the substituting amino acid is selected from the group consisting of Ala, Arg, Asn, Asp, Cys, Gln, Glu, Gly, Phe, His, Ile, Lys, Met, Pro, Ser, Thr, Trp, Tyr, and Val;

(vii) when a substitution occurs at position 76, the substituting amino acid is selected from the group consisting of Ala, Arg, Cys, Ile, Leu, Met, Gln, Ser, Thr, Trp, Tyr, and Val;

(viii) when a substitution occurs at position 77, the substituting amino acid is selected from the group consisting of Ala, Arg, Cys, Gln, Glu, Gly, Phe, His, Ile, Lys, Leu, Met, Pro, Ser, Thr, Trp, Tyr, and Val;

(ix) when a substitution occurs at position 78, the substituting amino acid is selected from the group consisting of Ala, Arg, Asn, Asp, Cys, Gln, Glu, Gly, Phe, His, Ile, Lys, Leu, Met, Pro, Thr, Trp, Tyr, and Val;

(x) when a substitution occurs at position 79, the substituting amino acid is selected from the group consisting of Ala, Arg, Asn, Asp, Cys, Gln, Gly, Phe, His, Lys, Leu, Met, Pro, Ser, Thr, Trp, Tyr, and Val;

(xi) when a substitution occurs at position 80, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val;

(xii) when a substitution occurs at position 81, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr;

(xiii) when a substitution occurs at position 82, the substituting amino acid is selected from the group consisting of Ala, Arg, Asn, Asp, Cys, Gln, Glu, Gly, Phe, His, Ile, Lys, Met, Pro, Ser, Thr, Trp, Tyr, and Val;

(xiv) when a substitution occurs at position 83, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val; and (xv) when a substitution occurs at position 84, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr.

Still more preferably in this embodiment, when a substitution occurs in the third epitope region, the substitution occurs at one or more of positions 70, 71, 72, 73, 74, 75, 76, 77, 78, 79, 80, 81, 82, 83, and 84 wherein:

(i) when a substitution occurs at position 70, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val;

(ii) when a substitution occurs at position 71, the substituting amino acid is selected from the group consisting of Ala, Arg, Asn, Cys, Gln, Gly, Phe, His, Ile, Lys, Leu, Met, Pro, Ser, Trp, Tyr, and Val;

(iii) when a substitution occurs at position 72, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr;

(iv) when a substitution occurs at position 73, the substituting amino acid is selected from the group consisting of Arg, Asn, Asp, Cys, Glu, Gly, Phe, His, Ile, Lys, Met, Pro, Ser, Thr, Trp, Tyr, and Val;

(v) when a substitution occurs at position 74, the substituting amino acid is selected from the group consisting of Arg, Asn, Asp, Cys, Gln, Glu, Gly, Phe, His, Ile, Lys, Leu, Met, Ser, Thr, Trp, Tyr, and Val;

(vi) when a substitution occurs at position 75, the substituting amino acid is selected from the group consisting of Ala, Arg, Asn, Asp, Cys, Gln, Glu, Gly, Phe, His, Ile, Lys, Met, Ser, Thr, Trp, Tyr, and Val;

(vii) when a substitution occurs at position 76, the substituting amino acid is selected from the group consisting of Ala, Arg, Cys, Ile, Leu, Met, Gln, Ser, Thr, Trp, Tyr, and Val;

(viii) when a substitution occurs at position 77, the substituting amino acid is selected from the group consisting of Ala, Arg, Cys, Gln, Glu, Gly, Phe, His, Ile, Lys, Leu, Met, Pro, Ser, Thr, Trp, Tyr, and Val;

(ix) when a substitution occurs at position 78, the substituting amino acid is selected from the group consisting of Ala, Arg, Asn, Asp, Cys, Gln, Glu, Gly, Phe, His, Ile, Lys, Leu, Met, Pro, Thr, Trp, Tyr, and Val;

(x) when a substitution occurs at position 79, the substituting amino acid is selected from the group consisting of Ala, Arg, Asn, Cys, Gln, Gly, Phe, His, Lys, Leu, Met, Pro, Ser, Thr, Trp, Tyr, and Val;

(xi) when a substitution occurs at position 80, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val;

(xii) when a substitution occurs at position 81, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr;

(xiii) when a substitution occurs at position 82, the substituting amino acid is selected from the group consisting of Ala, Arg, Asn, Asp, Cys, Gln, Glu, Gly, Phe, His, Ile, Lys, Met, Pro, Ser, Thr, Trp, Tyr, and Val;

(xiv) when a substitution occurs at position 83, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val; and (xv) when a substitution occurs at position 84, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr.

Most preferably, wherein one or more substitutions occurs in the third epitope region, the variants of the present invention comprise a substitution of one or more of positions 73, 74, 75, 76, 77, 78, 79, 80, 81, 82, 83 (73–83), even more preferably one or more of 75, 76, 77, 78, 79, 80, 81, 82 (75–82), and most preferably 78 or 79.

One or more additional substitution mutations ("stabilizing substitutions") may additionally be made at any position of the serine protease in order to, for example, restabilize the protease upon mutation of the epitope region or to enhance the proteolytic activity of the variant. Many such stabilizing mutations are well known in the art. Examples of such stabilizing mutations are disclosed in, for example, WO 95/10591, Baeck et al., published Apr. 20, 1995; U.S. Pat. No. 4,914,031, Zukowski et al., issued Apr. 3, 1990; U.S. Pat. No. 5,470,733, Bryan et al., issued Nov. 28, 1995; U.S. Pat. No. 5,567,601, Bryan et al., issued Oct. 22, 1996; WO 89/07642, U.S. Pat. No. 5,707,848, Bryan et al., issued Jan. 13, 1998; Van Eekelen et al., published Aug. 24, 1989; WO 87/04461, Stabinsky et al., published Jul. 30, 1987; U.S. Pat. No. 4,760,025, Estell et al., issued Jul. 26, 1988; WO 92/11348, Branner et al., published Jul. 9, 1992; EP 0,405,901, Casteleijn et al., published Jan. 2, 1991; WO 91/00345, Branner et al., published Jan. 10, 1991; and WO 94/10020, Brode et al., published Mar. 23, 1995.

Preferred stabilizing mutations include one or more of: I107V; K213R; Y217L; Y217K; N218S; G169A; M50F; Q19E; P5A; S9A; I31L; E156S; G169A; N212G; S188P; T254A; S3C+Q206C; and Q271E. The more preferred stabilizing mutations include one or more of P5A; S9A; I31L; E156S; G169A; N212G; S188P; T254A; S3C+Q206C; Q271E; Y217L; and Y217K. The most preferred stabilizing mutations include Y217L and Y217K.

Method of Making

The variants are prepared by mutating the nucleotide sequences that code for a wild-type serine protease, thereby resulting in variants having modified amino acid sequences. Such methods are well-known in the art; one such method is set forth below:

A phagemid (pSS-5) containing the wild-type subtilisin BPN' gene (Mitchison, C. and J. A. Wells, "Protein Engineering of Disulfide Bonds in Subtilisin BPN'", *Biochemistry*, Vol. 28, pp. 4807–4815 (1989) is transformed into *Escherichia coli* dut-ung-strain CJ236 and a single stranded uracil-containing DNA template is produced using the VCSM13 helper phage (Kunkel et al., "Rapid and Efficient Site-Specific Mutagenesis Without Phenotypic Selection", *Methods in Enzymology*, Vol 154, pp. 367–382 (1987), as modified by Yuckenberg et al., "Site-Directed in vitro Mutagenesis Using Uracil-Containing DNA and Phagemid Vectors", *Directed Mutagenesis—A Practical Approach*, McPherson, M. J. ed., pp. 27–48 (1991). Primer site-directed mutagenesis modified from the method of Zoller and Smith (Zoller, M. J., and M. Smith, "Oligonucleotide—Directed Mutagenesis Using M13—Derived Vectors: An Efficient and General Procedure for the Production of Point Mutations in any Fragment of DNA", *Nucleic Acids Research*, Vol. 10, pp. 6487–6500 (1982) is used to produce all mutants (essentially as presented by Yuckenber et al., supra).

Oligonucleotides are made using a 380B DNA synthesizer (Applied Biosystems Inc.). Mutagenesis reaction products are transformed into *Escherichia coli* strain MM294 (American Type Culture Collection *E. coli* 33625). All mutations are confirmed by DNA sequencing and the isolated DNA is transformed into the Bacillus subtilis expression strain PG632 (Saunders et al., "Optimization of the Signal-Sequence Cleavage Site for Secretion from Bacillus subtilis of a 34-amino acid Fragment of Human Parathyroid Hormone", *Gene*, Vol. 102, pp. 277–282(1991) and Yang et al., "Cloning of the Neutral Protease Gene of *Bacillus subtilis* and the Use of the Cloned Gene to Create an in vitro-Derived Deletion Mutation", *Journal of Bacteriology*, Vol. 160, pp. 15–21(1984). Preliminary assessment of variant activity is determined by the ability of PG632 cells transformed with mutant plasmids to hydrolyze casein.

Fermentation is as follows. *Bacillus subtilis* cells (PG632) containing the variant of interest are grown to mid-log phase in one liter of LB broth containing 10 g/L glucose, and inoculated into a Biostat C fermentor (Braun Biotal Inc., Allentown, Pa.) in total volume of 9 liters. The fermentation medium contains yeast extract, casein hydrosylate, soluble—partially hydrolyzed starch (Maltrin M-250), antifoam, buffers, and trace minerals (see "Biology of Bacilli: Applications to Industry", Doi, R. H. and M. McGloughlin, eds. (1992)). The broth is kept at a constant pH of 7.5 during the fermentation run. Kanamycin (50 $\mu$g/mL) is added for antibiotic selection of the mutagenized plasmid. The cells are grown for 18 hours at 37° C. to an $A_{600}$ of about 60 and the product harvested.

The fermentation broth is taken through the following steps to obtain pure variant. The broth is cleared of *Bacillus subtilis* cells by tangential flow against a 0.16 $\mu$m membrane. The cell-free broth is then concentrated by ultrafiltration with a 8000 molecular weight cut-off membrane. The pH is adjusted to 5.5 with concentrated MES buffer (2-(N-morpholino)ethanesulfonic acid). The variant is further purified by cation exchange chromatography with S-sepharose and elution with NaCl gradients. (see Scopes, R. K., "Protein Purification Principles and Practice", Springer-Verlag, New York (1984).

A pNA assay (DelMar et al., *Analytical Biochemistry*, Vol. 99, pp. 316–320 (1979)) is used to determine the active variant concentration for fractions collected during gradient elution. This assay measures the rate at which p-nitroaniline is released as the variant hydrolyzes the soluble synthetic substrate, succinyl-alanine-alanine-proline-phenylalanine-p-nitroaniline (sAAPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the variant purity, and is used to identify fractions to be pooled for the stock solution.

To avoid autolysis of the variant during storage, an equal weight of propylene glycol is added to the pooled fractions obtained from the chromatography column. Upon completion of the purification procedure the purity of the stock variant solution is checked with SDS-PAGE (sodium dodecyl sulfate polyacrylamide gel electrophoresis) and the absolute enzyme concentration is determined via an active site titration method using trypsin inhibitor type II-T: turkey egg white (Sigma Chemical Co., St. Louis, Mo.).

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M tris buffer (tris (hydroxymethyl-aminomethane) containing 0.01M $CaCl_2$ and pH adjusted to 8.6 with HCl. All experiments are carried out at pH 8.6 in tris buffer thermostated at 25° C.

Analytical Methods

The present variants may be tested for enzymatic activity and immune and/or allergenic response using the following methods, both of which are known to one skilled in the art. Alternatively, other methods well-known in the art may be used.

Variant Activity

The protease activity of a variant of the present invention may be assayed by methods which are well-known in the art. Two such methods are set forth herein below:

Skin Flake Activity Method

Using Scotch® #3750G tape, human skin flakes are stripped from the legs of a subject epeatedly until the tape is substantially opaque with flakes. The tape is then cut into 1 inch by 1 inch squares and set aside. In a 10 mm by 35 mm petri dish, 2 mL of 0.75 mg/mL of a control enzyme (for example, subtilisin BPN') or the variant to be tested is added in 0.01 M $KH_2PO_4$ pH 5.5 buffer. To this solution 1 mL of 2.5% sodium laurate pH 8.6 solution is added. The solution is gently mixed on a platform shaker. The previously prepared tape square is soaked in the solution (flake side up) for ten minutes continuing gentle mixing. The tape square is then rinsed gently in tap water for fifteen seconds. Stevenel Blue Stain (3 mL, commercially available from Sigma Chemical Co., St. Louis, Mo.) is pipetted into a clean petri dish. The rinsed tape square is placed into the stain for three minutes (flake side up) with gentle mixing. The tape square is removed from the stain and rinsed consecutively in two beakers of 300 mL distilled water, for fifteen seconds per rinse. The tape square is allowed to air-dry. The color intensity between the tape square obtained from the control enzyme and the tape square obtained from the variant is compared visually or by using a chromameter. Relative to the control enzyme tape square, a variant tape square showing less color intensity is indicative of a variant having higher activity.

Dyed Collagen Activity Method

Combine 50 mL of 0.1 M tris buffer (tris-hydroxymethyl-aminomethane) containing 0.01 M $CaCl_2$ to give pH 8.6, and 0.5 g azocoll (azo dye impregnated collagen, commercially available from Sigma Chemical Co., St. Louis, Mo.). Incubate this mixture at 25° C. while gently mixing with a platform shaker. Filter 2 mL of the mixture through a 0.2 micron syringe filter and read absorbance of the mixture at 520 nm to zero a spectrophotometer. Add 1 ppm of a control enzyme (for example, subtilisin BPN') or the variant to be tested to the remaining 48 mL of tris/azocoll mixture. Filter 2 mL of the control/variant containing solution through a 0.2 micron syringe filter every two minutes for a total of ten minutes. For each filtered sample, read the absorbance immediately at 520 nm. Plot the results against time. The slopes of the control and the test conjugate are indicative of relative activities of the samples. A higher slope is indicative of a higher activity. The test variant activity (slope) may be expressed as a percent of the control activity (slope).

Mouse Intranasal Test for Immunogenicity

The immunogenic potential of the serine protease variants of the present invention may be determined using a methods known in the art or by the Mouse Intranasal Test for Immunogenicity presented herein below. This test is similar to the assays described in Robinson et al., "Specific Antibody Responses to Subtilisin Carlsberg (Alcalase) in Mice: Development of an Intranasal Exposure Model", *Fundamental and Applied Toxicology*, Vol. 34, pp. 15–24 (1996) and Robinson et al., "Use of the Mouse Intranasal Test (MINT) to Determine the Allergenic Potency of Detergent Enzymes: Comparison to the Guinea Pig Intratracheal (GPIT) Test", *Toxicological Science*, Vol. 43, pp. 39–46 (1998), both of which assays may be utilized in place of the test set forth herein below.

Female BDK1 mice(Charles River Laboratories, Portage, Mich.) weighing from about 18 to about 20 grams are utilized in the test. The mice are quarantined one week prior to dosing. The mice are housed in cages with wood chip bedding in rooms controlled for humidity (30–70%), temperature (67–77° F.) and 12 hour light and dark cycles. The mice are fed Purina® mouse chow (Purina Mills, Richmond, Ind.) and water *ad libitum.*

The potential antigen to be tested (either subtilisin BPN' as positive control or a variant of the present invention) is dosed to a group of five mice. Prior to dosing, each mouse is anesthetized by an intraperitoneal (i.p.) injection of a mixture of Ketaset (88.8 mg/kg) and Rompun (6.67 mg/kg). The anesthetized animal is held in the palm of the hand, back down, and dosed intranasally with 5 mL protease in buffer solution (0.01 M $KH_2PO_4$, pH 5.5). While each group receives the same dosage, various dosages may be tested. Dosing solutions are gently placed on the outside of each nostril and inhaled by the mouse. Dosing is repeated on days 3, 10, 17, and 24.

Serum samples are collected on day 29. Enzyme-specific IgG1 antibody in mouse serum is measured by an antigen capture ELISA method. Immunogenicities of the variant may be compared against those of subtilisin BPN' using standard $ED_{50}$ values.

Compositions of the Present Invention

The variants herein can be used in any application which is suitable for the respective wild-type protease. One such example includes cleaning compositions. Because of the desirable reduced allergenicity and/or immunogenicity properties of the present variants, the variants may further be used in applications which have minimally benefited from the use of proteases. Examples of such applications include those in which the variant necessarily comes in close contact with human skin, such as with the use of personal care compositions.

Cleaning Compositions

The variants may be utilized in cleaning compositions including, but not limited to, laundry compositions, hard surface cleansing compositions, light duty cleaning compositions including dish cleansing compositions, and automatic dishwasher detergent compositions.

The cleaning compositions herein comprise an effective amount of one or more variants of the present invention and a cleaning composition carrier.

As used herein, "effective amount of variant", or the like, refers to the quantity of variant necessary to achieve the proteolytic activity necessary in the specific cleaning composition. Such effective amounts are readily ascertained by one of ordinary skill in the art and is based on many factors, such as the particular variant used, the cleaning application, the specific composition of the cleaning composition, and whether a liquid or dry (e.g., granular, bar) composition is desired, and the like. Preferably, the cleaning compositions comprise from about 0.0001% to about 10%, more preferably from about 0.001% to about 1%, and most preferably from about 0.01% to about 0.1% of one or more variants of the present invention. Several examples of various cleaning compositions wherein the variants may be employed are discussed in further detail below.

In addition to the present variants, the present cleaning compositions further comprise a cleaning composition carrier comprising one or more cleaning composition materials compatible with the variant. The term "cleaning composition material", as used herein, means any material selected for the particular type of cleaning composition desired and the form of the product (e.g., liquid, granule, bar, spray, stick, paste, gel), which materials are also compatible with the variant used in the composition. The specific selection of cleaning composition materials is readily made by considering the material to be cleaned, the desired form of the composition for the cleaning condition during use. The term "compatible", as used herein, means the cleaning composition materials do not reduce the proteolytic activity of the variant to such an extent that the variant is not effective as desired during normal use situations. Specific cleaning composition materials are exemplified in detail hereinafter.

The variants of the present invention may be used in a variety of detergent compositions where high sudsing and good cleansing activity is desired. Thus, the variants can be used with various conventional ingredients to provide fully-formulated hard-surface cleaners, dishwashing compositions, fabric laundering compositions, and the like. Such compositions can be in the form of liquids, granules, bars, and the like. Such compositions can be formulated as "concentrated" detergents which contain as much as from about 30% to about 60% by weight of surfactants.

The cleaning compositions herein may optionally, and preferably, contain various surfactants (e.g., anionic, nonionic, or zwitterionic surfactants). Such surfactants are typically present at levels of from about 5% to about 35% of the compositions.

Nonlimiting examples of surfactants useful herein include the conventional $C_{10}$–$C_{18}$ alkyl benzene sulfonates and primary and random alkyl sulfates, the $C_{10}$–$C_{18}$ secondary (2,3) alkyl sulfates of the formulas $CH_3(CH_2)_x(CHOSO_3)^- M^+)CH_3$ and $CH_3(CH_2)_y(CHOSO_3^- M^+) CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ a-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. The use of such surfactants in combination with the amine oxide and/or betaine or sultaine surfactants is also preferred, depending on the desires of the formulator. Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993.

A wide variety of other ingredients useful in detergent cleaning compositions can be included in the compositions herein including, for example, other active ingredients, carriers, hydrotropes, processing aids, dyes or pigments, and solvents for liquid formulations. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additional sudsing.

The liquid detergent compositions herein may contain water and other solvents as carriers. Low molecular weight primary or secondary alcohols exemplified by methanol, ethanol, propanol, and iso-propanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11. Finished products are typically formulated at this range. Techniques for controlling pH at recommended usage levels include the use of, for example, buffers, alkalis, and acids. Such techniques are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Soil release agents, especially of the anionic oligoester type, chelating agents, especially the aminophosphonates and ethylenediaminedisuccinates, clay soil removal agents, especially ethoxylated tetraethylene pentamine, dispersing agents, especially polyacrylates and polyasparatates, brighteners, especially anionic brighteners, suds suppressors, especially silicones and secondary alcohols, fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

The present variants are useful in hard surface cleaning compositions. As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more variants of the present invention, preferably from about 0.001% to about 10%, more preferably from about 0.01% to about 5%, more preferably still from about 0.05% to about 1% by weight of variant of the composition. In addition to comprising one or more of the variants, such hard surface cleaning compositions typically comprise a surfactant and a water-soluble sequestering builder. In certain specialized products such as spray window cleaners, however, the surfactants are sometimes not used since they may produce a filmy and/or streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of from about 7 to about 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, more preferably from about 3% to about 11%.

Additionally, highly volatile solvents such as iso-propanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

Hard surface cleaning compositions of the present invention are illustrated by the following examples.

EXAMPLES 1–6

Liquid Hard Surface Cleaning Compositions

| | Ex. 1 | Ex. 2 | Ex. 3 | Ex. 4 | Ex. 5 | Ex. 6 |
|---|---|---|---|---|---|---|
| Variant N109A | 0.05% | 0.50% | 0.02% | 0.03% | 0.30% | 0.05% |
| EDTA | — | — | 2.90% | 2.90% | — | — |
| Sodium Citrate | — | — | — | — | 2.90% | 2.90% |

-continued

Liquid Hard Surface Cleaning Compositions

| | Ex. 1 | Ex. 2 | Ex. 3 | Ex. 4 | Ex. 5 | Ex. 6 |
|---|---|---|---|---|---|---|
| $NaC_{12}$ Alkyl-benzene sulfonate | 1.95% | — | 1.95% | — | 1.95% | — |
| $NaC_{12}$ Alkyl-sulfate | — | 2.20% | — | 2.20% | — | 2.20% |
| $NaC_{12}$ (ethoxy) sulfate | — | 2.20% | — | 2.20% | — | 2.20% |
| $C_{12}$Dimethyl-amine oxide | — | 0.50% | — | 0.50% | — | 0.50% |
| Sodium cumene sulfonate | 1.30% | — | 1.30% | — | 1.30% | — |
| Hexyl Carbitol | 6.30% | 6.30% | 6.30% | 6.30% | 6.30% | 6.30% |
| Water | 90.4% | 88.3% | 87.53% | 85.87% | 87.25% | 85.85% |

All formulas are adjusted to pH 7.

In another embodiment of the present invention, dishwashing compositions comprise one or more variants of the present invention. As used herein, "dishwashing composition" refers to all forms of compositions for cleaning dishes including, but not limited to, granular and liquid forms. Dishwashing compositions of the present invention are illustrated by the following examples.

EXAMPLES 7–10

Liquid Dish Detergent

| | Ex. 7 | Ex. 8 | Ex. 9 | Ex. 10 |
|---|---|---|---|---|
| Variant I115A | 0.05% | 0.50% | 0.02% | 0.40% |
| $C_{12}$–$C_{14}$ N-methyl glucamide | 0.90% | 0.90% | 0.90% | 0.90% |
| $C_{12}$ ethoxy(1)sulfate | 12.0% | 12.0% | 12.0% | 12.0% |
| 2-Methyl undecanoic acid | 4.50% | 4.50% | 4.50% | 4.50% |
| $C_{12}$ ethoxy (2) carboxylate | 4.50% | 4.50% | 4.50% | 4.50% |
| $C_{12}$ alcohol ethoxylate (4) | 3.00% | 3.00% | 3.00% | 3.00% |
| $C_{12}$ amine oxide | 3.00% | 3.00% | 3.00% | 3.00% |
| Sodium cumene sulfonate | 2.00% | 2.00% | 2.00% | 2.00% |
| Ethanol | 4.00% | 4.00% | 4.00% | 4.00% |
| $Mg^{2+}$ (as $MgCl_2$) | 0.20% | 0.20% | 0.20% | 0.20% |
| $Ca^{2+}$ (as $CaCl_2$) | 0.40% | 0.40% | 0.40% | 0.40% |
| Water | 65.45% | 65% | 65.48% | 65.1% |

All formulas are adjusted to pH 7.

Liquid fabric cleaning compositions of the present invention are illustrated by the following examples.

EXAMPLES 11–13

Liquid Fabric Cleaning Compositions

| | Ex. 11 | Ex. 12 | Ex. 13 |
|---|---|---|---|
| Variant A116V | 0.05% | 0.03% | 0.30% |
| Sodiuam $C_{12}$–$C_{14}$ alkyl sulfate | 20.0% | 20.0% | 20.0% |
| 2-Butyl octanoic acid | 5.0% | 5.0% | 5.0% |
| Sodium citrate | 1.0% | 1.0% | 1.0% |
| $C_{10}$ Alcohol ethoxylate (3) | 13.0% | 13.0% | 3.0% |
| Monoethanolamine | 2.50% | 2.50% | 2.50% |
| Water/propylene glycol/ethanol (100:1:1) | 58.45% | 58.47% | 58.20% |

Personal Care Compositions

The present variants are particularly suited for use in personal care compositions such as, for example, leave-on and rinse-off hair conditioners, shampoos, leave-on and rinse-off acne compositions, facial milks and conditioners, shower gels, soaps, foaming and non-foaming facial cleansers, cosmetics, hand, facial, and body lotions and moisturizers, leave-on facial moisturizers, cosmetic and cleansing wipes, oral care compositions, and contact lens care compositions. The present personal care compositions comprise one or more variants of the present invention and a personal care carrier.

To illustrate, the present variants are suitable for inclusion in the compositions described in the following references: U.S. Pat. No. 5,641,479, Linares et al., issued Jun. 24, 1997 (skin cleansers); U.S. Pat. No. 5,599,549, Wivell et al., issued Feb. 4, 1997 (skin cleansers); U.S. Pat. No. 5,585,104, Ha et al., issued Dec. 17, 1996 (skin cleansers); U.S. Pat. No. 5,540,852, Kefauver et al., issued Jul. 30, 1996 (skin cleansers); U.S. Pat. No. 5,510,050, Dunbar et al., issued Apr. 23, 1996 (skin cleansers); U.S. Pat. No. 5,612,324, Guang Lin et al., issued Mar. 18, 1997 (anti-acne preparations); U.S. Pat. No. 5,587,176, Warren et al., issued Dec. 24, 1996 (anti-acne preparations); U.S. Pat. No. 5,549,888, Venkateswaran, issued Aug. 27, 1996 (anti-acne preparations); U.S. Pat. No. 5,470,884, Corless et al., issued Nov. 28, 1995 (anti-acne preparations); U.S. Pat. No. 5,650,384, Gordon et al., issued Jul. 22, 1997 (shower gels); U.S. Pat. No. 5,607,678, Moore et al., issued Mar. 4, 1997 (shower gels); U.S. Pat. No. 5,624,666, Coffindaffer et al., issued Apr. 29, 1997 (hair conditioners and/or shampoos); U.S. Pat. No. 5,618,524, Bolich et al., issued Apr. 8, 1997 (hair conditioners and/or shampoos); U.S. Pat. No. 5,612,301, Inman, issued Mar. 18, 1997 (hair conditioners and/or shampoos); U.S. Pat. No. 5,573,709, Wells, issued Nov. 12, 1996 (hair conditioners and/or shampoos); U.S. Pat. No. 5,482,703, Pings, issued Jan. 9, 1996 (hair conditioners and/or shampoos); U.S. Pat. No. Re. 34,584, Grote et al., Reissued Apr. 12, 1994 (hair conditioners and/or shampoos); U.S. Pat. No. 5,641,493, Date et al., issued Jun. 24, 1997 (cosmetics); U.S. Pat. No. 5,605,894, Blank et al., issued Feb. 25, 1997 (cosmetics); U.S. Pat. No. 5,585,090, Yoshioka et al., issued Dec. 17, 1996 (cosmetics); U.S. Pat. No. 4,939,179, Cheney et al., issued Jul. 3, 1990 (hand, face, and/or body lotions); U.S. Pat. No. 5,607,980, McAtee et al., issued Mar. 4, 1997 (hand, face, and/or body lotions); U.S. Pat. No. 4,045,364, Richter et al., issued Aug. 30, 1977 (cosmetic and cleansing wipes); European Patent Application, EP 0 619 074, Touchet et al., published Oct. 12, 1994 (cosmetic and cleansing wipes); U.S. Pat. No. 4,975,217, Brown-Skrobot et al., issued Dec. 4, 1990 (cosmetic and cleansing wipes); U.S Pat. No. 5,096,700, Seibel, issued Mar. 17, 1992 (oral cleaning compositions); U.S. Pat. No. 5,028,414, Sampathkumar, issued Jul. 2, 1991 (oral cleaning compositions); U.S. Pat. No. 5,028,415, Benedict et al., issued Jul. 2, 1991 (oral cleaning compositions); U.S. Pat. No. 5,028,415, Benedict et al., issued Jul. 2, 1991 (oral cleaning compositions); U.S. Pat. No. 4,863,627, Davies et al., Sep. 5, 1989 (contact lens cleaning solutions); U.S. Pat. No. Re. 32,672, Huth et al, reissued May 24, 1988 (contact lens cleaning solutions); and U.S. Pat. No. 4,609,493, Schafer, issued Sep. 2, 1986 (contact lens cleaning solutions).

To further illustrate oral cleaning compositions of the present invention, a pharmaceutically-acceptable amount of one or more variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in the references cited herein above.

In another embodiment of the present invention, denture cleaning compositions for cleaning dentures outside of the oral cavity comprise one or more variants of the present invention. Such denture cleaning compositions comprise an effective amount of one or more of the variants, preferably from about 0.0001% to about 50% of one or more of the variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see, e.g., U.S. Pat. No. 5,055,305, Young), and are generally appropriate for incorporation of one or more of the variants for removing proteinaceous stains from dentures.

In another embodiment of the present invention, contact lens cleaning compositions comprise one or more variants of the present invention. Such contact lens cleaning compositions comprise an effective amount of one or more of the variants, preferably from about 0.01% to about 50% of one or more of the variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art and are generally appropriate for incorporation of one or more variants of the present invention for removing proteinaceous stains from contact lenses.

The contact lens cleaning composition embodiment of the present invention is illustrated by Examples 14–17.

EXAMPLES 14–17

| Contact Lens Cleaning Solution | Ex. 14 | Ex. 15 | Ex. 16 | Ex. 17 |
|---|---|---|---|---|
| Variant M119A | 0.01% | 0.5% | 0.1% | 2.0% |
| Glucose | 50.0% | 50.0% | 50.0% | 50.0% |
| Nonionic surfactant (polyoxyethlene-pol | 2.0% | 2.0% | 2.0% | 2.0% |
| Anionic surfactant (polyoxyethylene-alkylphenylether sodium sulfricester) | 1.0% | 1.0% | 1.0% | 1.0% |
| Sodium Chloride | 1.0% | 1.0% | 1.0% | 1.0% |
| Borax | 0.30% | 0.30% | 0.30% | 0.30% |
| Water | 45.69% | 45.20% | 45.60% | 43.70% |

Examples 18–21 illustrate the use of the present variants in bodywash products:

EXAMPLES 18–21

| Bodywash Products | Ex. 18 | Ex. 19 | Ex. 20 | Ex. 21 |
|---|---|---|---|---|
| Water | 62.62% | 65.72% | 57.72% | 60.72% |
| Disodium EDTA | 0.2% | 0.2% | 0.2% | 0.2% |
| Glycerine | 3.0% | 3.0% | 3.0% | 3.0% |
| Polyquaternium 10 | 0.4% | 0.4% | 0.4% | 0.4% |
| Sodium laureth sulphate | 12.0% | 12.0% | 12.0% | 12.0% |
| Cocamide MEA | 2.8% | 2.8% | 2.8% | 2.8% |
| Sodium lauraphoacetate | 6.0% | 6.0% | 6.0% | 6.0% |
| Myristic Acid | 1.6% | 1.6% | 1.6% | 1.6% |
| Magnesium sulphate heptahydrate | 0.3% | 0.3% | 0.3% | 0.3% |
| Trihydroxystearin | 0.5% | 0.5% | 0.5% | 0.5% |
| PEG-6 caprylic/capric triglycerides | 3.0% | — | — | — |
| Sucrose polyesters of cottonate fatty acid | 3.0% | — | — | — |
| Sucrose polyesters of behenate fatty acid | 3.0% | — | 4.0% | — |
| Petrolatum | — | 4.0% | 8.0% | — |
| Mineral Oil | — | — | — | 6.0% |
| DMDM Hydantoin | 0.08% | 0.08% | 0.08% | 0.08% |
| Variant D120A | 0.1% | 2.0% | 2.0% | 5.0% |
| Citric Acid | 1.40% | 1.40% | 1.40% | 1.40% |

Examples 22–25 illustrate the use of the present variants in facewash products:

EXAMPLES 22–25

| Facewash Products | Ex. 22 | Ex. 23 | Ex. 24 | Ex. 25 |
|---|---|---|---|---|
| Water | 66.52% | 65.17% | 68.47% | 68.72% |
| Disodium EDTA | 0.1% | 0.1% | 0.2% | 0.2% |
| Citric Acid | — | — | 1.4% | 1.4% |
| Sodium Laureth-3 Sulfate | 3.0% | 3.5% | — | — |
| Sodium Laureth-4 Carboxylate | 3.0% | 3.5% | — | — |
| Laureth-12 | 1.0% | 1.2% | — | — |
| Polyquaternium 10 | — | — | 0.4% | 0.4% |
| Polyquaternium 25 | 0.3% | 0.3% | — | — |
| Glycerine | 3.0% | 3.0% | 3.0% | 3.0% |
| Sodium Lauroamphoacetate | — | — | 6.0% | 6.0% |
| Lauric Acid | 6.0% | 6.0% | 3.0% | 3.0% |
| Myristic Acid | — | — | 3.0% | 3.0% |
| Magnesium sulphate heptahydrate | 2.3% | 2.0% | 2.0% | 2.0% |
| Triethanol amine | 4.0% | 4.0% | 4.0% | 4.0% |
| Trihydroxystearin | 0.5% | 0.5% | 0.5% | 0.5% |
| Sucrose polyesters of behenate | 2.0% | 2.0% | — | — |

-continued

Facewash Products

| | Ex. 22 | Ex. 23 | Ex. 24 | Ex. 25 |
|---|---|---|---|---|
| fatty acid | | | | |
| Sucrose polyesters of cottonate fatty acid | 3.0% | 2.0% | — | — |
| PEG-6 caprylic/capric triglycerides | — | — | — | 2.0% |
| Petrolatum | — | — | 4.0% | — |
| Mineral Oil | — | — | — | 2.0% |
| Cocamidopropyl betaine | 2.0% | 3.0% | 1.8% | 1.8% |
| Lauryl dimethylamine oxide | 1.0% | 1.2% | 1.2% | 1.2% |
| Dex Panthenol | 1.0% | 0.25% | 0.25% | — |
| DMDM Hydantoin | 0.08% | 0.08% | 0.08% | 0.08% |
| Variant A114* | 1.0% | 2.0% | 0.5% | 0.5% |
| Fragrance | 0.2% | 0.2% | 0.2% | 0.2% |

Examples 26–27 illustrate the use of the present variants in leave-on skin moisturizing compositions:

EXAMPLES 26–27

Leave-on Skin Moisturizing Composition

| | Ex. 26 | Ex. 27 |
|---|---|---|
| Glycerine | 5.0% | — |
| Stearic acid | 3.0% | — |
| $C_{11-13}$ Isoparaffin | 2.0% | — |
| Glycol stearate | 1.5% | — |
| Propylene glycol | — | 3.0% |
| Mineral oil | 1.0% | 10.0% |
| Sesame oil | — | 7.0% |
| Petrolatum | — | 1.8% |
| Triethanolamine | 0.7% | — |
| Cetyl acetate | 0.65% | — |
| Glyceryl stearate | 0.48% | 2.0% |
| TEA stearate | — | 2.5% |
| Cetyl alcohol | 0.47% | — |
| Lanolin alcohol | — | 1.8% |
| DEA-cetyl phosphate | 0.25% | — |
| Methylparaben | 0.2% | 0.2% |
| Propylparaben | 0.12% | 0.1% |
| Carbomer 934 | 0.11% | — |
| Disodium EDTA | 0.1% | — |
| Variant N117A | 0.1% | 0.5% |
| Water | 84.32% | 71.1% |

Example 28 illustrates the use of the present variants in cleansing wipe compositions:

EXAMPLE 28

Cleansing Wipe Composition

| | |
|---|---|
| Propylene Glycol | 1.0% |
| Ammonium lauryl sulfate | 0.6% |
| Succinic acid | 4.0% |
| Sodium succinate | 3.2% |
| Triclosan ® | 0.15% |
| Variant I122A | 0.05% |
| Water | 91.0% |

The above composition is impregnated onto a woven absorbent sheet comprised of cellulose and/or polyester at about 250%, by weight of the absorbent sheet.

What is claimed is:

1. A serine protease variant having a modified amino acid sequence of a wild-type amino acid sequence, the wild-type sequence comprising a first epitope region and a second epitope region, wherein the modified amino acid sequence comprises a substitution by a substituting amino acid at one or more positions in one or more of the epitope regions, wherein:

(a) when a substitution occurs in the first epitope region, the substitution occurs at a position corresponding to position 125 of the amino acid sequence of subtilisin BPN' set forth in SEQ ID NO:1, wherein:

(i) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr; and (b) when a substitution occurs in the second epitope region, the substitution occurs at a position corresponding to position 225 of the amino acid sequence of subtilisin BPN' set forth in SEQ ID NO:1, wherein:

(i) when a substitution occurs at position 225, the substituting amino acid is selected from the group consisting of Cys, Asp, Phe, Gly, His, Ile, Asn, Thr, Trp, and Tyr.

2. A serine protease variant having a modified amino acid sequence of a wild-type amino acid sequence, the wild-type sequence comprising a first epitope region and a second epitope region, wherein the modified amino acid sequence comprises a substitution by a substituting amino acid at two or more positions in one or more of the epitope regions, wherein:

(a) when a substitution occurs in the first epitope region, the substitution occurs at two or more of positions selected from the group of positions corresponding to positions consisting of 111 and 125 of the amino acid sequence of subtilisin BPN' set forth in SEQ ID NO:1, wherein:

(i) when a substitution occurs at position 111, the substituting amino acid is selected from the group consisting of Ala, Cys, Asp, Glu, Phe, Gly, His, Lys, Leu, Met, Asn, Pro, Gln, Arg, Ser, Thr, Val, Trp, and Tyr;

(ii) when a substitution occurs at position 125, the substituting amino acid is selected from the group consisting of Ala, Cys, Asp, Glu, Phe, Gly, His, Ile, Lys, Leu, Met, Asn, Pro, Gln, Arg, Thr, Val, Trp, and Tyr; and (b) when a substitution occurs in the second epitope region, the substitution occurs at two or more of positions selected from the group of positions corresponding to positions consisting of 225 and 242 of the amino acid sequence of subtilisin BPN' set forth in SEQ ID NO:1, wherein:

(i) when a substitution occurs at position 225, the substituting amino acid is selected from the group consisting of Cys, Asp, Phe, Gly, His, Ile, Asn, Thr, Trp, and Tyr;

(ii) when a substitution occurs at position 242, the substituting amino acid is selected from the group consisting of Ala, Cys, Asp, Glu, Phe, Gly, His, Ile, Lys, Leu, Met, Asn, Gln, Arg, Ser, Val, Trp, and Tyr.

3. A variant according to claim 1 wherein the serine protease is selected from the group consisting of subtilisin BPN', subtilisin Carlsberg, subtilisin DY, subtilisin 309, proteinase K, and thermitase.

4. A variant according to claim 3 further comprising one or more stabilizing mutations.

5. A variant according to claim 2 wherein the modified amino acid sequence comprises a substitution by a substituting amino acid at three or more positions in one or more of the epitope regions.

6. A variant according to claim 5 wherein the modified amino acid sequence comprises a substitution by a substituting amino acid at four or more positions in one or more of the epitope regions.

7. A cleaning composition comprising a variant according to claim 1 and a cleaning composition carrier.

8. A personal care composition comprising a variant according to claim 1 and a personal care carrier.

9. A variant according to claim 2 wherein the serine protease is selected from the group consisting of subtilisin BPN', subtilisin Carlsberg, subtilisin DY, subtilisin 309, proteinase K, and thermitase.

10. A variant according to claim 9 further comprising one or more stabilizing mutations.

11. A cleaning composition comprising a variant according to claim 2 and a cleaning composition carrier.

12. A personal care composition comprising a variant according to claim 2 and a personal care carrier.

* * * * *

UNITED STATES PATENT AND TRADEMARK OFFICE

CERTIFICATE OF CORRECTION

PATENT NO. : 6,586,223 B1 Page 1 of 1
DATED : July 1, 2003
INVENTOR(S) : Sikorski et al.

It is certified that error appears in the above-identified patent and that said Letters Patent is hereby corrected as shown below:

Column 3,
Line 44, "Vol. 11" should read -- Vol. II --.

Column 5,
Line 23, "110" should read -- 111 --.

Column 27,
Line 4, "Yuckenber" should read -- Yuckenberg --.
Line 24, "Biotal" should read -- Biotech, --.

Column 28,
Line 25, "epeatedly" should read -- repeatedly --.

Column 29,
Line 17, "BDK1" should read -- BDF1 --.
Line 17, "mice(Charles" should read -- mice (Charles --.

Column 30,
Line 45, "$C_{10}$-$C_{18}$" should read -- $C_{11}$-$C_{18}$ --.

Column 33,
Line 63, "$C_{10}$ Alcohol ethocylate (3) 13.0% 13.0% 3.0%" should read
-- $C_{10}$ Alcohol ethocylate (3) 13.0% 13.0% 13.0% --.

Signed and Sealed this

Twenty-eighth Day of October, 2003

JAMES E. ROGAN
*Director of the United States Patent and Trademark Office*